(12) United States Patent
Kesten et al.

(10) Patent No.: US 10,130,799 B2
(45) Date of Patent: Nov. 20, 2018

(54) INFLATOR WITH VARYING MECHANICAL ADVANTAGE

(71) Applicant: Acclarent, Inc., Menlo Park, CA (US)

(72) Inventors: Randy J. Kesten, Mountain View, CA (US); Arthur M. Lin, Fremont, CA (US); Scott O. Chamness, Menlo Park, CA (US)

(73) Assignee: Acclarent, Inc., Irvine, CA (US)

( * ) Notice: Subject to any disclaimer, the term of this patent is extended or adjusted under 35 U.S.C. 154(b) by 720 days.

(21) Appl. No.: 14/469,867

(22) Filed: Aug. 27, 2014

(65) Prior Publication Data

US 2016/0058988 A1    Mar. 3, 2016

(51) Int. Cl.
| | |
|---|---|
| *A61M 25/10* | (2013.01) |
| *A61B 17/24* | (2006.01) |
| *A61M 25/00* | (2006.01) |
| *A61M 29/02* | (2006.01) |
| *A61M 3/02* | (2006.01) |

(Continued)

(52) U.S. Cl.
CPC ....... *A61M 25/10182* (2013.11); *A61B 17/24* (2013.01); *A61M 3/0295* (2013.01); *A61M 5/31511* (2013.01); *A61M 25/0097* (2013.01); *A61M 25/10184* (2013.11);
(Continued)

(58) Field of Classification Search
CPC ...... A61M 25/1018–25/10188; A61M 3/0295; A61M 5/178; A61M 5/3129; A61M 5/315; A61M 5/31501; A61M 5/31526; A61M 2005/3143; A61M 2025/1022; A61M 2005/3152; A61M 5/31573; A61M 5/31575; A61M 5/31581; A61M 5/31528
See application file for complete search history.

(56) References Cited

U.S. PATENT DOCUMENTS

| | | | | |
|---|---|---|---|---|
| 4,064,879 A | * | 12/1977 | Leibinsohn | A61M 5/486 604/121 |
| 4,759,750 A | * | 7/1988 | DeVries | A61M 5/315 116/DIG. 17 |

(Continued)

OTHER PUBLICATIONS

Zarebski, Igor, and Tadeusz Salacinski. "Designing of Non-Circular Gears." The Archive of Mechanical Engineering, LV, 2008, prozamet.pl/art_2008_3_08.pdf.*

(Continued)

*Primary Examiner* — Andrew Gilbert
*Assistant Examiner* — James D Ponton
(74) *Attorney, Agent, or Firm* — Frost Brown Todd LLC

(57) ABSTRACT

An inflator comprises a body, a first drive member, and a second drive member. The body defines a reservoir that is configured to hold fluid and includes an outlet. The first drive member is operable to move through the reservoir to drive fluid from the reservoir through the outlet. The second drive member is engaged with the first drive member. The second drive member is movable relative to the body through a first range of motion to actuate the first drive member to drive fluid through the outlet at a first rate. The second drive member is movable relative to the body through a second range of motion following the first range of motion. The first drive member is configured to either drive fluid through the outlet at a second rate or not drive fluid through the outlet as the second drive member moves through the second range of motion.

20 Claims, 34 Drawing Sheets

(51) Int. Cl.
*A61M 5/315* (2006.01)
*A61M 29/00* (2006.01)

(52) U.S. Cl.
CPC ......... *A61M 29/02* (2013.01); *A61M 5/31575* (2013.01); *A61M 29/00* (2013.01); *A61M 2210/0681* (2013.01)

(56) References Cited

U.S. PATENT DOCUMENTS

| | | | |
|---|---|---|---|
| 5,057,078 A * | 10/1991 | Foote | A61M 5/315 604/224 |
| 5,507,727 A * | 4/1996 | Crainich | A61M 25/10182 604/209 |
| 7,630,676 B2 | 12/2009 | Pirwitz | |
| 8,105,171 B2 | 1/2012 | Murakami | |
| 8,568,446 B2 | 10/2013 | Kurokawa et al. | |
| 9,155,492 B2 | 10/2015 | Jenkins et al. | |
| 2002/0004651 A1 * | 1/2002 | Ljunggreen | A61M 5/31501 604/218 |
| 2008/0183128 A1 | 7/2008 | Morriss et al. | |
| 2010/0030031 A1 | 2/2010 | Goldfarb et al. | |
| 2011/0004057 A1 | 1/2011 | Goldfarb et al. | |
| 2011/0288478 A1 * | 11/2011 | Ehrenreich | A61M 25/10181 604/99.04 |
| 2013/0211374 A1 * | 8/2013 | Hetherington | A61B 17/8822 604/506 |
| 2014/0074141 A1 | 3/2014 | Johnson et al. | |
| 2014/0081205 A1 * | 3/2014 | Kanner | A61M 25/1018 604/97.02 |
| 2015/0328405 A1 * | 11/2015 | Metzner | A61M 5/20 604/143 |
| 2016/0045718 A1 * | 2/2016 | Pruitt | A61M 25/10182 604/97.02 |

OTHER PUBLICATIONS

International Search Report and Written Opinion dated Sep. 18, 2015 for Application No. PCT/US2015/044627, 9 pgs.

* cited by examiner

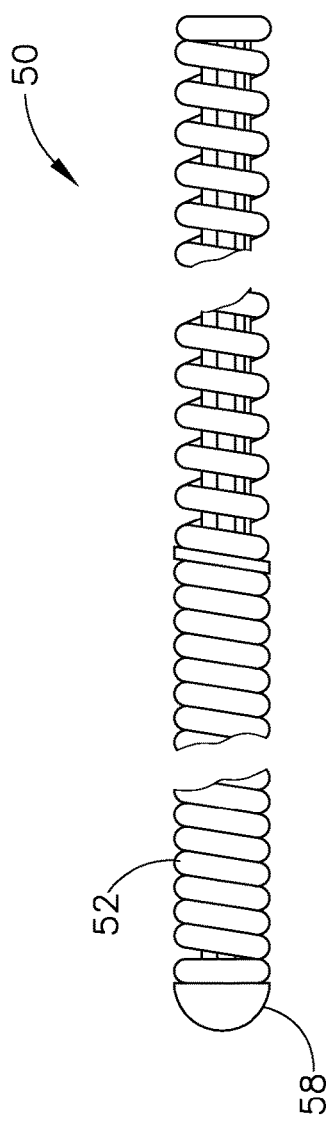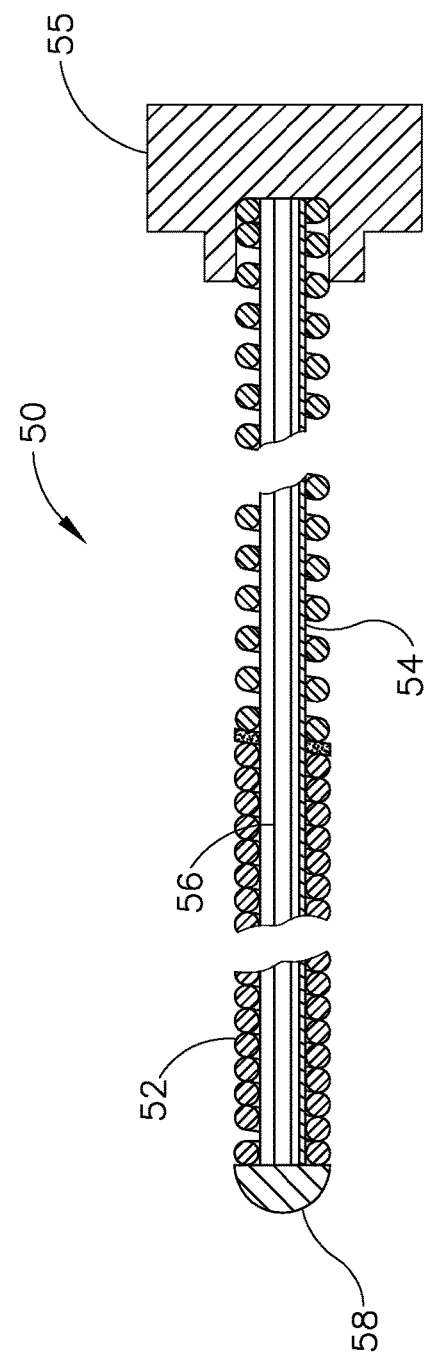
Fig. 2
Fig. 3

INFLATOR WITH VARYING MECHANICAL ADVANTAGE

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, now U.S. Pat. No. 9,155,492, issued Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

It may be desirable to provide easily controlled inflation/deflation of a balloon in dilation procedures, including procedures that will be performed only by a single operator. While several systems and methods have been made and used to inflate an inflatable member such as a dilation balloon, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 2 depicts a side elevational view of an exemplary illuminating guidewire suitable for use with the dilation catheter system of FIG. 1;

FIG. 3 depicts a side cross-sectional view of the illuminating guidewire of FIG. 2;

Figure 1:
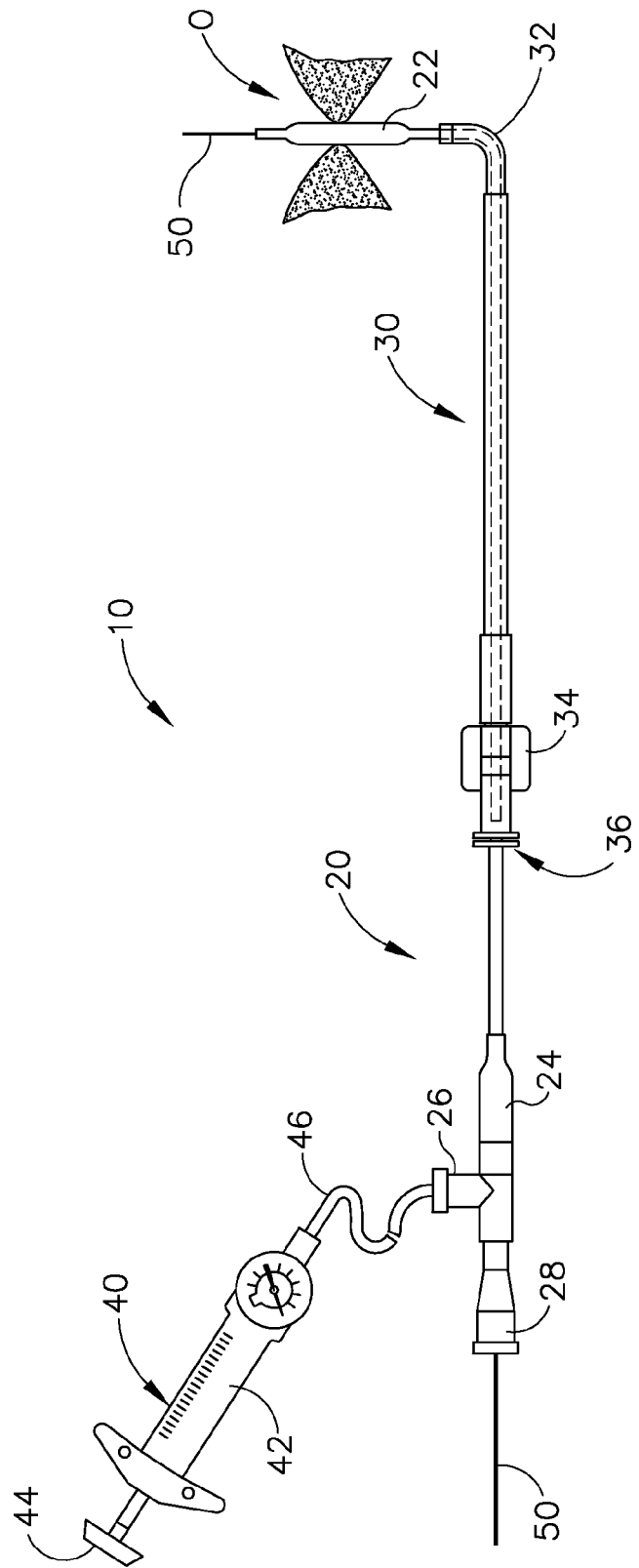
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

The distal end of dilation catheter (20) includes an inflatable dilator (22). The proximal end of dilation catheter (20) includes a grip (24), which has a lateral port (26) and an open proximal end (28). Dilation catheter (20) includes a first lumen (not shown) that provides fluid communication between lateral port (26) and the interior of dilator (22). Dilator catheter (20) also includes a second lumen (not shown) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

Guide catheter (30) of the present example includes a bent distal end (32) and a grip (34) at its proximal end. Grip (34) has an open proximal end (36). Guide catheter (30) defines a lumen that is configured to slidably receive catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26).

As best seen in FIGS. 2-3, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, now U.S. Pat. No. 9,155,492, issued Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

In an exemplary dilation procedure, guide catheter (30) may first be positioned near the targeted anatomical passageway, such as a sinus ostium (O). Dilator (22) and the distal end of guidewire (50) may be positioned within or proximal to bent distal end (32) of guide catheter (30) at this stage. Guide catheter (30) is initially inserted into the nose of the patient and is advanced to a position that is within or near the ostium (O) to be dilated. This positioning of guide catheter (30) may be performed under visualization provided by an endoscope such as endoscope (60) described below. After guide catheter (30) has been positioned, the operator may advance guidewire (50) distally through guide catheter (30) such that a distal portion of the guidewire (50) passes through the sinus ostium (O) and into the sinus cavity. The operator may illuminate illumination fiber (56) and lens (58), which may provide transcutaneous illumination through the patient's face to enable the operator to visually confirm positioning of the distal end of guidewire (50) with relative ease.

With guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the sinus ostium (O) (or some other targeted anatomical passageway). After dilator (22) has been positioned within the ostium (O), dilator (22) may be inflated, thereby dilating the ostium. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient.

In some instances, it may be desirable to irrigate the sinus and paranasal cavity after dilation catheter (20) has been used to dilate an ostium (O). Such irrigation may be performed to flush out blood, etc. that may be present after the dilation procedure. By way of example only, such irrigation may be carried out in accordance with at least some of the teachings of U.S. Pub. No. 2008/0183128, entitled "Methods, Devices and Systems for Treatment and/or Diagnosis of Disorders of the Ear, Nose and Throat," published Jul. 31, 2008, now abandoned, the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

II. Overview of Exemplary Endoscope

Figure 4:
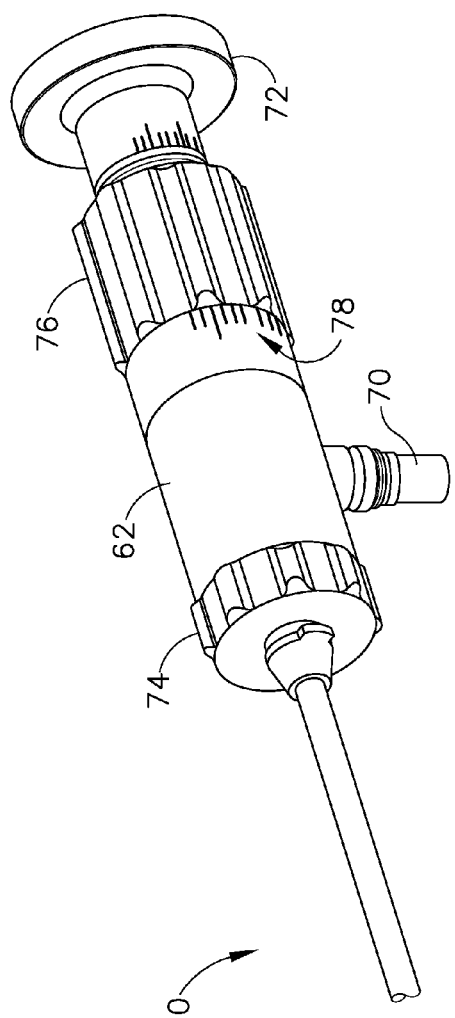
FIG. 4 depicts a perspective view of an exemplary endoscope suitable for use with the dilation catheter system of FIG. 1.
Figure 5:
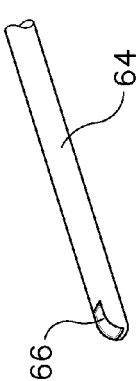
FIG. 5 depicts a side elevational view of the distal end of the endoscope of FIG. 4, showing an exemplary range of viewing angles.

As noted above, an endo scope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein III. Exemplary Alternative Inflators Inflator (40) shown in FIG. 1 and described above is just one example of an inflator that may be incorporated into dilator catheter system (10). Additional merely illustrative examples of alternative forms that inflator (40) may take will be described in greater detail below. It should be understood that these exemplary alternative inflators may be readily coupled with flexible tube (46) in place of inflator (40) described above, for use in dilator catheter system (10). In some versions, the exemplary alternative inflators described below may be directly coupled with lateral port (26), such that flexible tube (46) is simply omitted. Other suitable configurations and arrangements will be apparent to those of ordinary skill in the art in view of the teachings herein.

A. Exemplary Alternative Inflator with Knob and Push-button Thread Release

Figure 6:
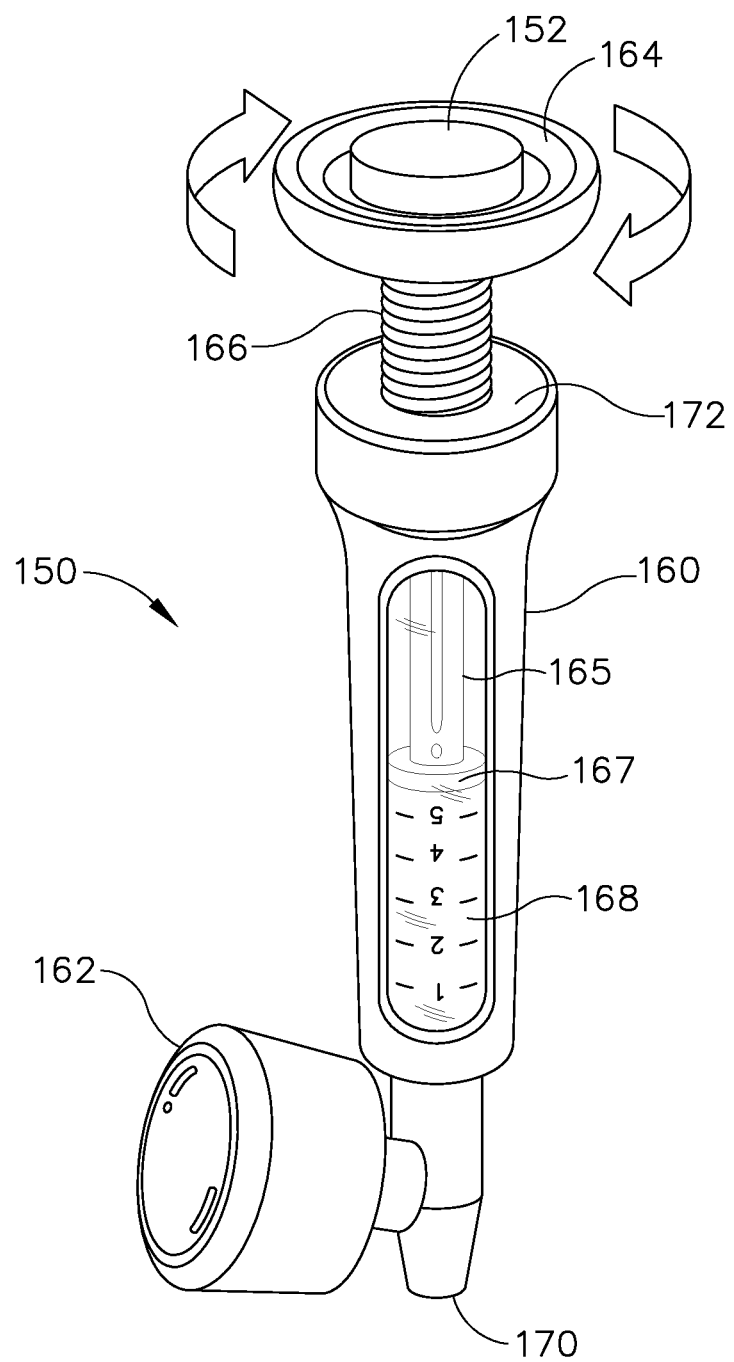
FIG. 6 depicts a perspective view of an exemplary inflator suited for use with the dilator catheter system of FIG. 1.
Figure 7:
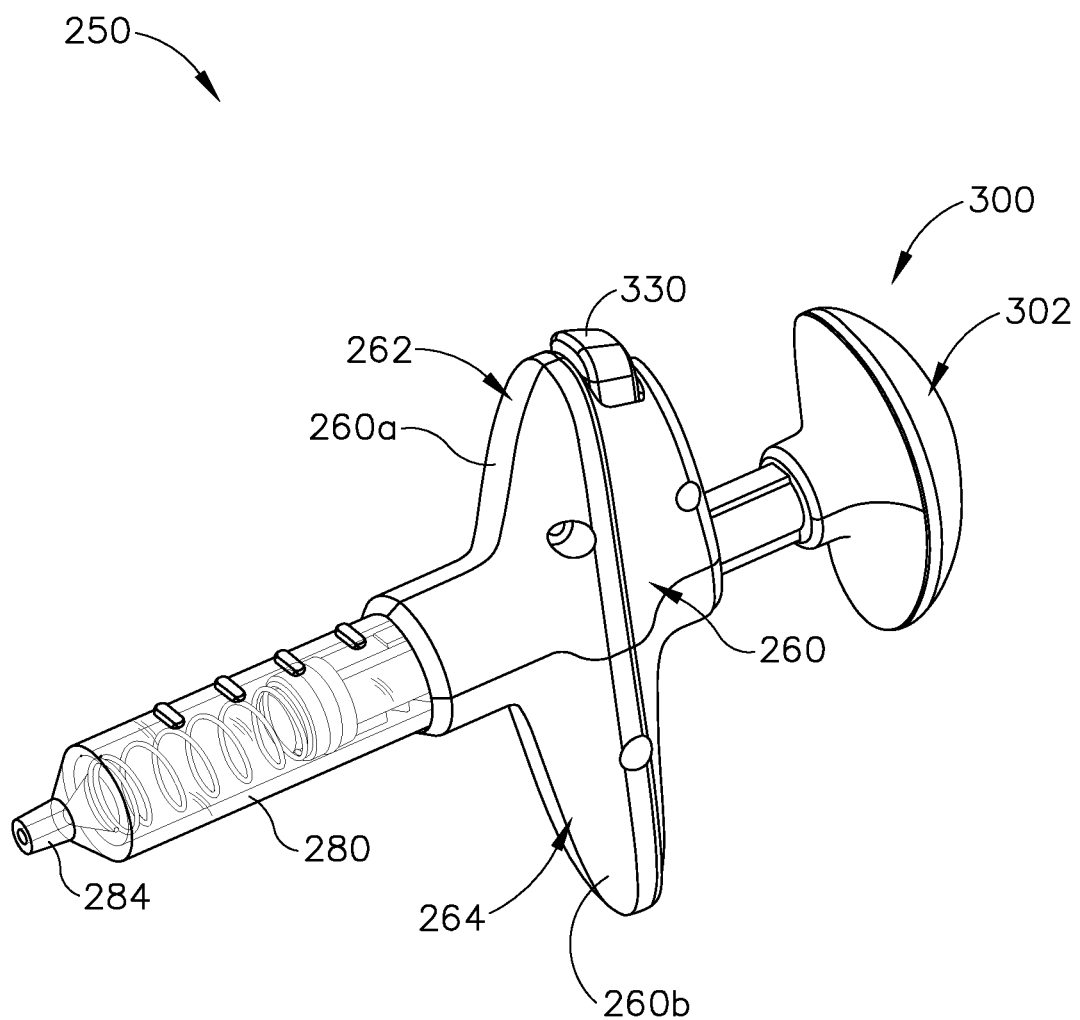
FIG. 7 depicts a perspective view of another exemplary inflator suited for use with the dilator catheter system of FIG. 1.

FIG. 6 shows an exemplary inflator (150) that comprises a body (160), an actuator knob (164), and a pressure gauge (162). Body (160) of the present example is formed as a substantially hollow cylinder, similar to syringe barrel (42) described above, although other suitable configurations may be used. Body (160) comprises a reservoir (168), a distal port (170), and a proximal cap (172). A rod (165) extends into body (160). Plunger (167) is coupled to a distal end of rod (165) and extends outwardly to the inner diameter of body (160) to form a substantially fluid tight seal with body (160). The volume between plunger (167) and the distal end of body (160) forms reservoir (168). Reservoir (168) may be configured to hold about 3 to about 5 cc of fluid (e.g., saline). Rod (165) and plunger (167) may translate proximally and distally to adjust the size of reservoir (168). When rod (165) and plunger (167) translate proximally, the volume of reservoir (168) increases. When rod (165) and plunger (167) translate distally, the volume of reservoir (168) decreases. Port (170) at the distal end of body (160) is in fluid communication with reservoir (168) such that fluid may flow into and out of reservoir (168) via port (170). Port (170) may be coupled with flexible tube (46) of dilator catheter system (10).

Actuator knob (164) is coupled to body (160) via a threaded shaft (166), which is in selective threaded engagement with proximal cap (172) of body (160). Threaded shaft (166) is configured to rotate unitarily with actuator knob (164). Thus, rotation of actuator knob (164) relative to body (160) will cause threaded shaft (166) to translate relative to body (160) when the threading of threaded shaft (166) is engaged with proximal cap (172). Threaded shaft (166) is further coupled with rod (165) such that when actuator knob (164) is rotated relative to body (160), rod (165) and plunger (167) translate proximally or distally relative to body (165) based on the direction in which actuator knob (164) and threaded shaft (166) are rotated. In some versions, threaded shaft (166) and rod (165) are the same structure, such that threaded shaft (166) extends all the way to plunger (167). In some such versions, threaded shaft (166) rotates freely relative to plunger (167).

In the present example, push button (152) is operable to disengage the threading of threaded shaft (166) relative to proximal cap (172), to thereby permit threaded shaft (166) to translate freely relative to body (160) when push button (152) is in a depressed position. Various suitable features that may be used to provide such operability will be apparent to those of ordinary skill in the art in view of the teachings herein. By way of example only, the threading of threaded shaft (166) may be selectively retractable inwardly relative to the longitudinal axis of threaded shaft (166). A translating cam component (not shown) that is coupled with push button (152) may be operable to extend and/or retract the threading of threaded shaft (166) based on the position of push button (152). For instance, when push button (152) is not being depressed, the cam component may be biased to a position where it urges the threading outwardly and holds the threading in the outward position, into engagement with threaded cap (172). The threading may itself be resiliently biased to retract inwardly, such that when push button (152) is depressed, the cam component disengages the threading and the threading retracts inwardly to disengage body (160). It should also be understood that push button (152) may be resiliently biased toward the non-depressed position. Still other suitable components and configurations that may be used to provide the above-described selective engagement between threaded shaft (166) and proximal cap (172) will be apparent to those of ordinary skill in the art in view of the teachings herein.

Gauge (162) of the present example is positioned distal of reservoir (168) to measure the pressure within dilator catheter system (10). Gauge (162) may include a pivoting pin that indicates fluid pressure based on the angular position of the pin. Alternatively, gauge (162) may provide any other suitable type of indication of fluid pressure, including but not limited to the other types of fluid pressure indication described below. In the present example, gauge (162) is operable to indicate pressure levels up to at least about 12 atmospheres. For instance, some uses of dilator catheter system (10) may include inflation of dilator (22) to a range between about 10 atmospheres and about 12 atmospheres in order to sufficiently dilate a targeted anatomical passageway. Gauge (162) may thus provide the operator with real time feedback indicating the fluid pressure within dilator (22) to enable the operator to determine whether the desired pressure level has been achieved.

In an exemplary use of inflator (150), a operator may start with plunger (167) advanced to a distal position in body (160). The operator may then position port (170) in a bowl or other container of saline to draw fluid from. In instances where port (170) is coupled with one end of flexible tube (46), the operator may position the other end of flexible tube (46) in the saline. In either case, the operator may then retract plunger (167) relative to body (160) to draw the saline (or other fluid) into reservoir (168). In some instances, the operator depresses button (152) to disengage threading of threaded shaft (166) from proximal cap (172), thereby permitting the operator to freely pull plunger (167) proximally without having to rotate actuator knob (164). The operator may nevertheless grasp actuator knob (164) in order to translate plunger (167) proximally. The operator may observe the position of plunger (167) relative to indicia on body (160) and may initially draw in more fluid than the operator expects to need in order to sufficiently inflate dilator (22). The operator may then remove port (170) or flexible tube (46) from the saline container and advance plunger (167) distally in order to purge air from reservoir (168). For instance, the operator may orient inflator (150) such that port (170) is positioned upwardly to gather air at the top of reservoir (168) before advancing plunger (167) distally in order to purge air from reservoir (168).

Once reservoir (168) has been sufficiently filled with fluid and air has been purged, the operator may couple inflator (150) with dilation catheter (20), such as by coupling port (170) with lateral port (26) via a flexible tube (46). With dilator (22) being suitably positioned within an anatomical passageway (e.g., an ostium (O), etc.), the operator may then advance plunger (167) distally in order to transfer fluid from reservoir (168) to dilator (22). In some instances, this act may begin with free translation of threaded shaft (166) relative to proximal cap (172), with the operator depressing push button (152) to disengage the threading, and with the operator gripping actuator knob (164) to translate threaded shaft (166) and plunger (167) distally. At some point, however, the operator may release push button (152) to engage the threading of threaded shaft (166) with proximal cap (172), and may finish the final stages of distal translation of plunger (167) by rotating actuator knob (164). This may enable the operator to more precisely "dial in" the appropriate amount of pressure in dilator (22), observing the pressure reading at gauge (162) while rotating actuator knob (164).

In some instances, the operator simply relies on tactile feedback in the form of physical resistance to pushing of actuator knob (164) in order to determine the appropriate time to transition from pushing of actuator knob (164) (with push button (152) depressed) to rotating of actuator knob (164) (with push button (152) released). In addition or in the alternative, the operator may determine the appropriate time to transition from pushing of actuator knob (164) to rotating of actuator knob (164) based on the position of plunger (167) relative to one or more markings on body (160). Other suitable forms of feedback that may be used to determine an appropriate transition time from pushing of actuator knob (164) to rotating of actuator knob (164) will be apparent to those of ordinary skill in the art in view of the teachings herein.

It should also be understood that the operator may rely on other kinds of feedback, in addition to or in lieu of feedback from gauge (162), in order to determine when to stop rotating actuator knob (164) during inflation of dilator (22). For instance, inflator (150) may include an indicator that corresponds to the torque level associated with rotation of actuator knob (164). The torque level may vary based on the fluid pressure in dilator (22), such that the torque level required to rotate actuator knob (164) increases as the fluid pressure in dilator (22) increases. A torque level indicator may thus serve as a fluid pressure indicator. By way of example only, the torque level indicator may provide audible and/or visual feedback indicating that a particular torque level (and, hence, fluid pressure level) has been achieved. In some versions, the torque level indicator provides a clicking sound. It should also be understood that the torque level indicator may provide substantially continuous feedback that changes with the torque level, such that the indicator provides a first sound associated with a first torque level and a second sound associated with a second torque level. Alternatively, the indicator may simply provide one form of feedback when one particular torque level is achieved (e.g., a torque level associated with 12 atmospheres of fluid pressure, etc.). The torque level indicator may also be adjustable such that the triggering torque level(s) and/or the type of feedback is/are selectable by an operator of inflator (150). Various suitable forms that a torque level indicator may take will be apparent to those of ordinary skill in the art in view of the teachings herein.

In addition to or in lieu of providing user feedback through gauge (162), a torque level indicator, and/or some other feature(s), inflator (150) may include a torque limiting feature that limits the amount of torque that may be applied through actuator knob (164). This may effectively restrict the amount of fluid pressure that may be created by inflator (150). Such a torque limiting feature may be adjustable, enabling the operator to preset a particular torque level (and, hence, preset a particular fluid pressure). Such a torque limiting feature may include a clutch mechanism, ball(s) in detent(s), pawl(s) and spring(s), frangible/shearable elements (e.g., shear pins), magnetic couplings, and/or various other components. As another merely illustrative example, such a torque limiting feature may be constructed in accordance with at least some of the teachings of U.S. Pat. No. 8,105,171, entitled "Torque Limiting Mechanism," issued Jan. 31, 2012, the disclosure of which is incorporated by reference herein. Other suitable forms that a torque limiting feature may take, as well as various ways in which a torque limiting feature may be incorporated into inflator (150), will be apparent to those of ordinary skill in the art in view of the teachings herein.

Once the operator has attained the desired level of pressure in dilator (22) within the anatomical passageway to dilate the anatomical passageway, the operator may pause for an approximate, predetermined period of time (e.g., approximately three seconds, etc.). The operator may then once again depress push button (152) and pull knob (164) proximally relative to body (160), to thereby retract plunger (167) for withdrawal of fluid from dilator (22). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (168) may be used repeatedly to dilate a plurality of anatomical passageways, without having to withdraw dilator (22) from the patient, and without having to decouple inflator (150) from the rest of dilator catheter system (10), until all of the desired dilations have been completed.

In the foregoing example, the threading of threaded shaft (166) is engaged with proximal cap (172) when push button (152) is not being depressed. In some other versions, the threading of threaded shaft (166) is engaged with proximal cap (172) only when push button (152) is being depressed. Other suitable variations of inflator (150) will be apparent to those of ordinary skill in the art in view of the teachings herein. Similarly, other suitable ways in which inflator (150) may be used will be apparent to those of ordinary skill in the art in view of the teachings herein.

B. Exemplary Alternative Inflator with Ratcheting Drive and Button Release

FIGS. 7-10E depict another exemplary inflator (250). Inflator (250) of this example includes a housing (260), a syringe barrel (280), and a plunger actuator (300). Housing (260) is formed by two halves (260a, 260b) that are joined together to contain syringe barrel (280) and plunger actuator (300). Housing (260) defines two finger grip features (262, 264) while the proximal end of plunger actuator (300) includes a palm grip feature (302). These grip features (262, 264, 302) are configured to enable a operator to grasp and manipulate inflator (250) with a single hand by wrapping their fingers about finger grip features (262, 264) while positioning palm grip feature (302) in the palm of the same hand. As will be described in greater detail below, inflator (250) may be selectively actuated by the operator squeezing their hand to drive plunger actuator (300) distally relative to housing (260); or by releasing their grip to enable plunger actuator (300) to retract proximally relative to housing (260).

Figure 8:
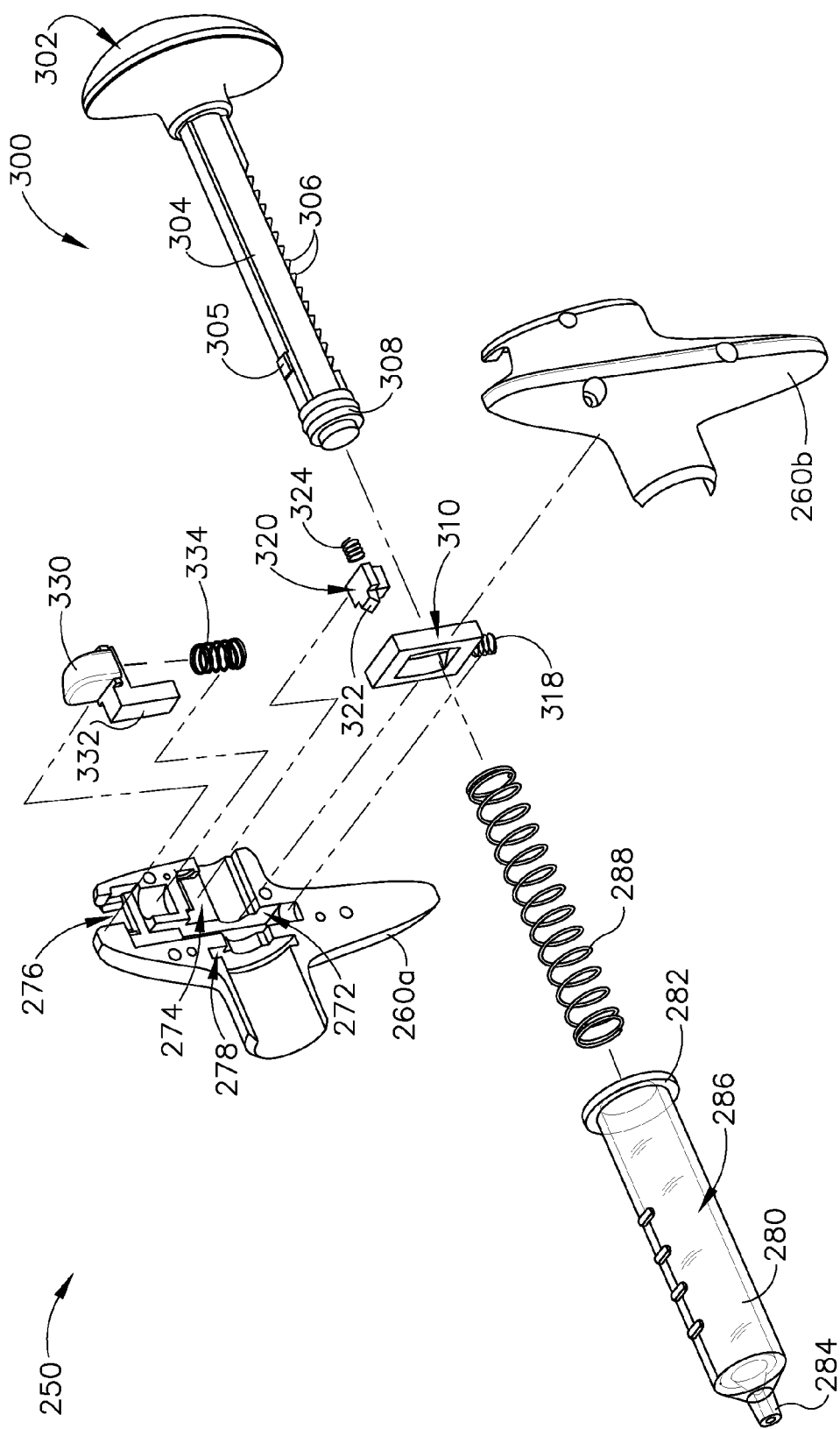
FIG. 8 depicts an exploded view of the inflator of FIG. 7.

As best seen in FIG. 8, each housing half (260a, 260b) defines a corresponding ratcheting block recess (272), a block latch recess (274), a pushbutton recess (276), and a flange recess (278). Ratcheting block recesses (272) cooperate to receive a ratcheting block (310) and associated spring (318). Spring (318) biases ratcheting block (310) upwardly within recess (272). Block latch recesses (274) cooperate to receive a block latch (320) and associated spring (324). Spring (324) biases block latch (320) distally within recess (274). Pushbutton recesses (276) cooperate to receive a pushbutton (330) and associated spring (334). Spring (334) biases pushbutton (330) upwardly within recess (272). While springs (318, 324, 334) all comprise coil springs in the present example, it should be understood that any other suitable types of resilient components or features may be used. Flange recesses (278) cooperate to receive upper flange (282) of syringe barrel (280), thereby fixedly securing syringe barrel (280) to housing (260). Other suitable features and configurations for housing (260) will be apparent to those of ordinary skill in the art in view of the teachings herein.

FIG. 8 also shows additional features of plunger actuator (300). In particular, plunger actuator (300) of this example comprises a shaft (304) extending distally from palm grip feature (302), with a set of sawteeth (306) on the underside of shaft (304). Shaft (304) also includes a latch engagement feature (305) projecting from the upper side of shaft (304). Latch engagement feature (305) is configured to interact with latch (320) as will be described in greater detail below. Shaft terminates in a piston (244), which is positioned within syringe barrel (280). Plunger actuator (300) is operable to translate relative to housing (260), to thereby reciprocate piston (244) within syringe barrel (280). It should be understood that such reciprocation will selectively vary the volume of reservoir (286) in syringe barrel (280), to thereby draw fluid into or expel fluid from reservoir (286). As shown in FIGS. 8 and 10A-10E, a spring (288) is positioned inside reservoir (286), between the distal face of piston (308) and the distal interior wall of reservoir (286), to bias plunger actuator (300) proximally relative to syringe barrel (280). While spring (288) comprises a coil spring in the present example, any other suitable type of resilient member may be used. Furthermore, spring (288) may be positioned elsewhere in inflator (250).

Figure 9:
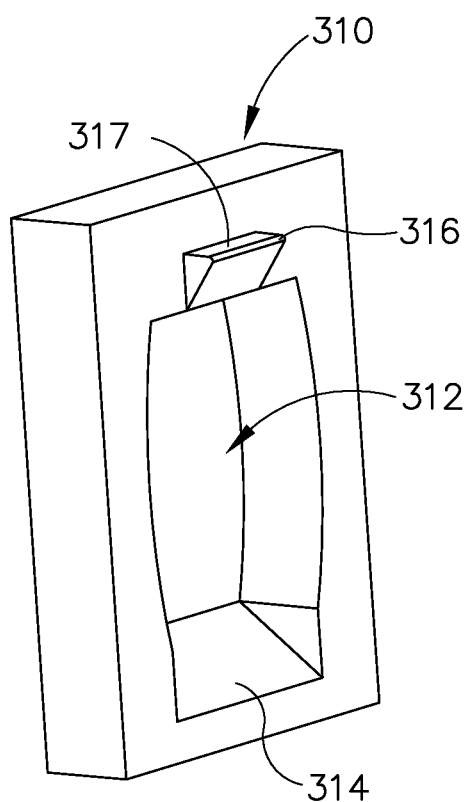
FIG. 9 depicts a perspective view of a ratchet block of the inflator of FIG. 7.

FIG. 9 shows the proximal side of ratcheting block (310). As shown, ratcheting block (310) defines an aperture (312) that is sized and configured to receive shaft (304) of plunger actuator (300). A pawl feature (314) is located at the bottom of aperture (312) and is shaped to complement sawteeth (306) of shaft (304). A latch cam feature (316) is located at the top of aperture (312) and is shaped to complement a cam feature (322) of block latch (320). As will be described in greater detail below, ratcheting block (310) is operable to permit plunger actuator (300) to freely translate from a proximal position to a distal position; while preventing plunger actuator (300) from retracting proximally when plunger actuator (300) is released during translation from the proximal position to the distal position. As will also be described in greater detail below, block latch (320) is configured to keep ratcheting block (310) disengaged from plunger actuator (300) after pushbutton (330) is actuated, until plunger actuator (300) reaches a proximal home position.

Figure 24A:
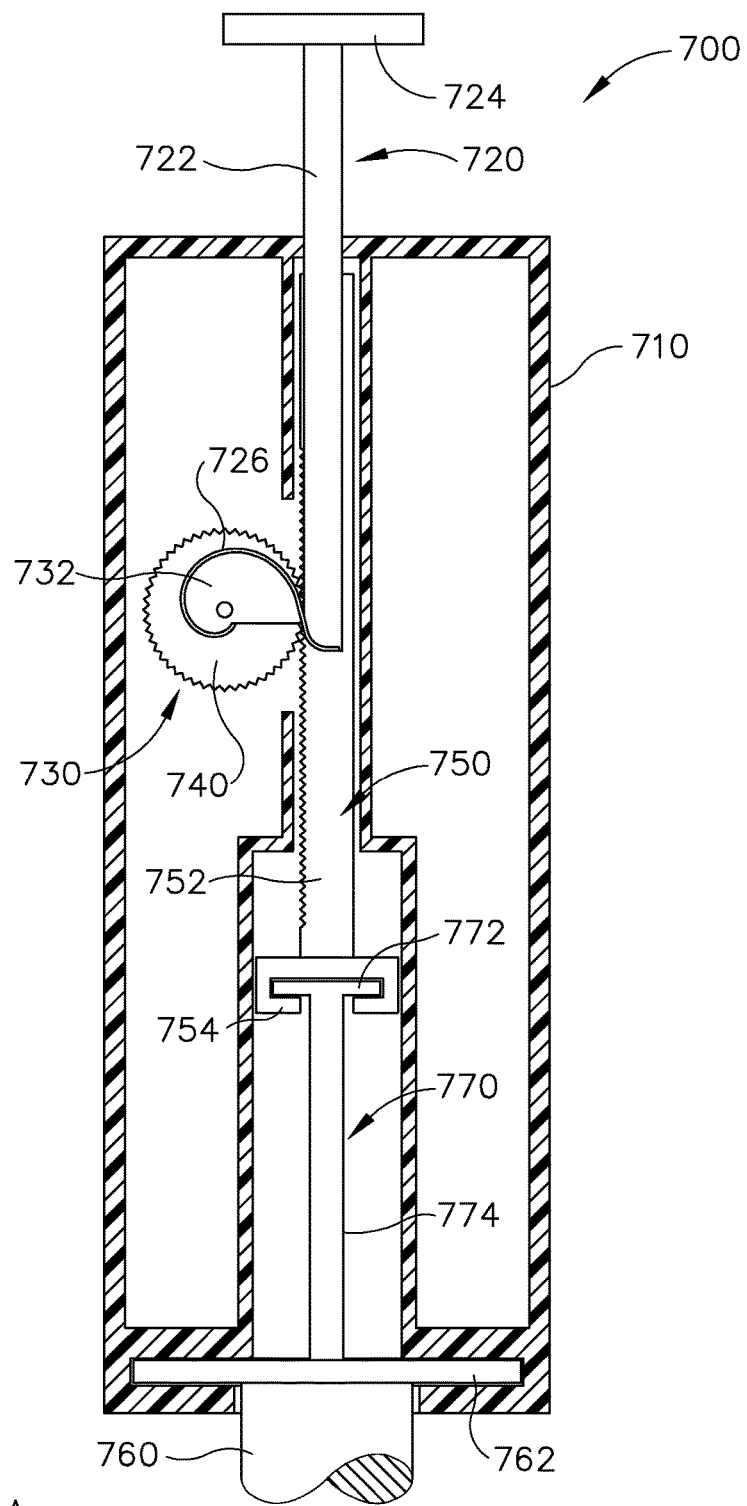
FIG. 24A depicts a side cross-sectional view of the inflator adapter of FIG. 20 coupled with a syringe assembly, with the inflator adapter in a non-actuated state.
Figure 24B:
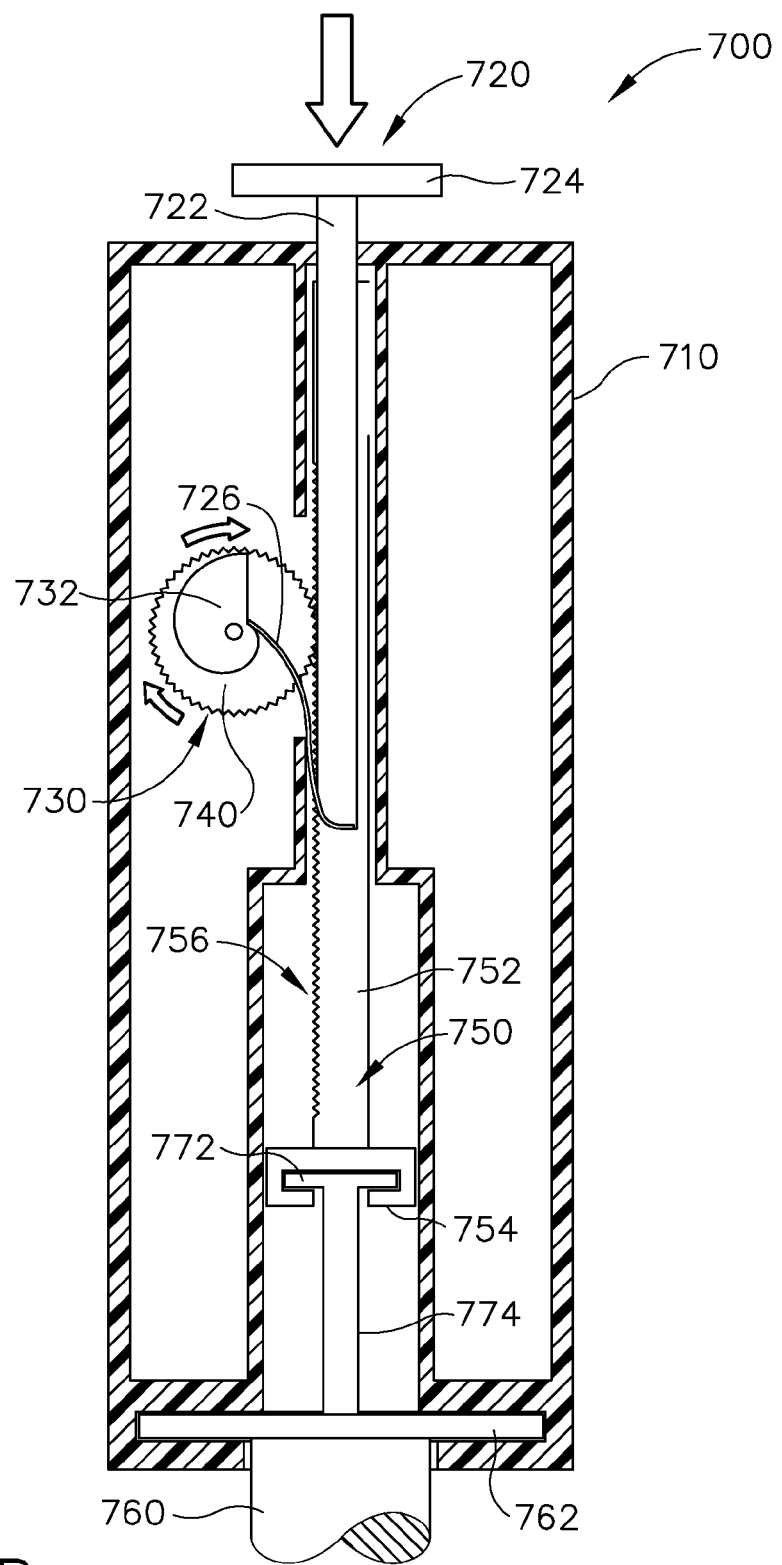
FIG. 24B depicts a side cross-sectional view of the inflator adapter of FIG. 20 coupled with a syringe assembly, with the inflator adapter in an actuated state.

FIGS. 10A-10E depict a series showing interactions between the above-described components during operation of inflator (250). In particular, FIG. 24A shows plunger actuator (300) in a proximal position. Ratcheting block (310) is in an upper position and pushbutton (330) is also in an upper position. Block latch (320) is in a distal position. FIG. 24B shows plunger actuator (300) advanced to a distal position. Ratcheting block (310) remains in an upper position, pushbutton (330) remains in an upper position, and block latch (320) remains in a distal position. During the advancement of plunger actuator (300) from the proximal position (FIG. 10A) to the distal position (FIG. 10B), pawl feature (314) ratchets along sawteeth (306) due to the resilient bias of spring (318). If the operator were to relax their grip on grip features (262, 264, 302) during advancement of plunger actuator (300), engagement between pawl feature (314) and sawteeth (306) would prevent plunger actuator (300) from moving proximally, despite the proximally directed bias from spring (288). Plunger actuator (300) would thus maintain its longitudinal position relative to housing (260) and also maintain its position after reaching the stage shown in FIG. 10B, until the operator depresses pushbutton (330).

Figure 10A:
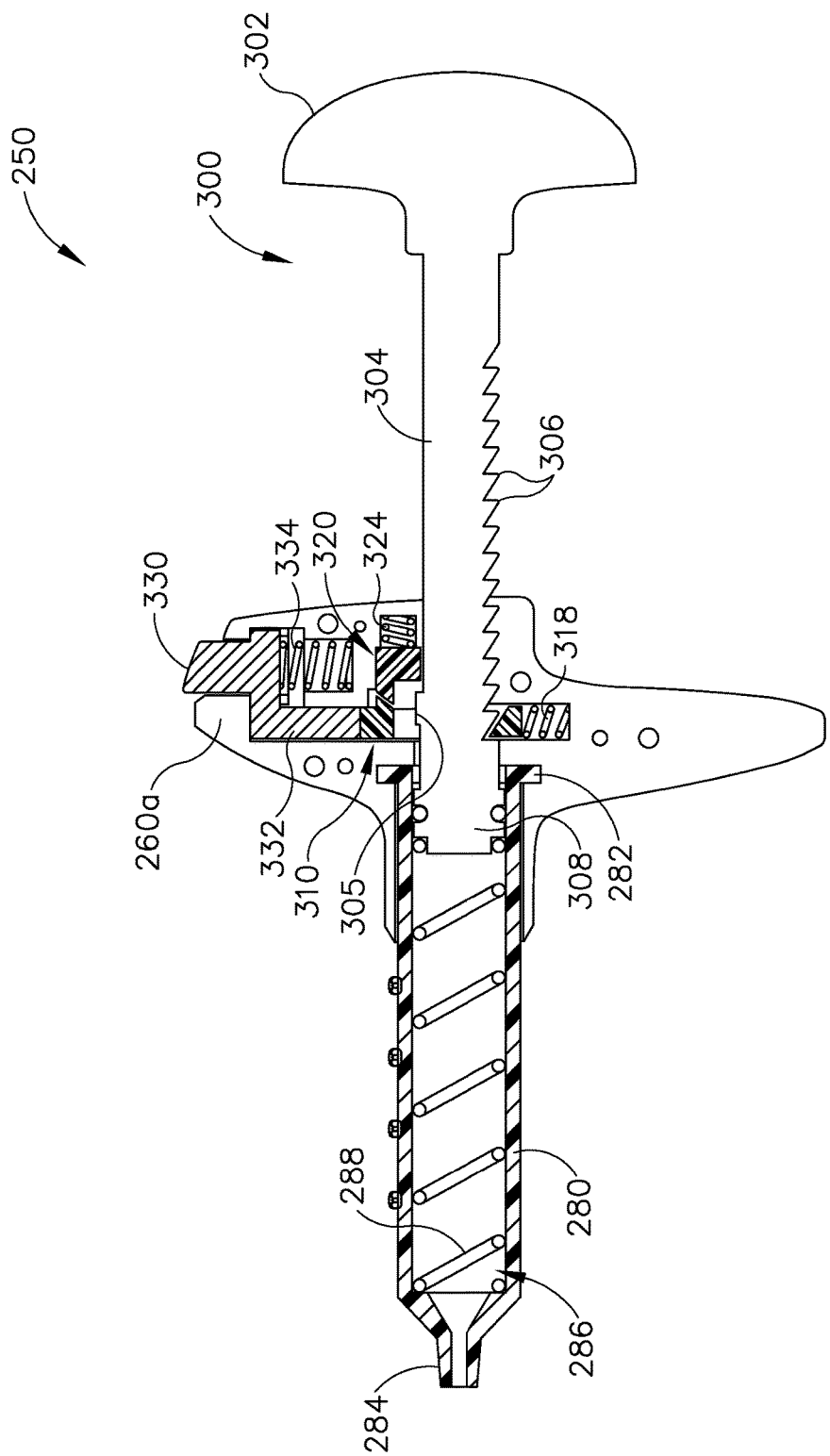
FIG. 10A depicts a cross-sectional side view of the inflator of FIG. 7, with the plunger in a proximal position.

Pushbutton (330) includes an integral, downwardly oriented projection (332) that is operable to drive ratcheting block (310) downwardly when pushbutton (330) is pushed downwardly. As shown in FIG. 10C, the resulting downward movement of ratcheting block (310) disengages pawl feature (314) from sawteeth (306). In addition, the downward movement of ratcheting block (310) results in camming interaction between cam features (316, 322). This camming interaction drives block latch (320) proximally until cam feature (316) moves downwardly past cam feature (322). As soon as cam feature (316) passes cam feature (322), spring (324) drives block latch (320) distally such that cam feature (322) is positioned over an upper shelf (317) of cam feature (316). This resulting arrangement prevents ratcheting block (310) from moving upwardly, such that block latch (320) effectively locks ratcheting block (310) in the downward position where pawl feature (314) is disengaged from sawteeth (306). This lock is maintained even after pushbutton (330) is released as shown in FIG. 10D. It should be understood that, at this stage, the only thing maintaining the longitudinal position of plunger actuator (300) relative to housing (260) is the operator's grip on grip features (262, 264, 302).

Figure 10B:
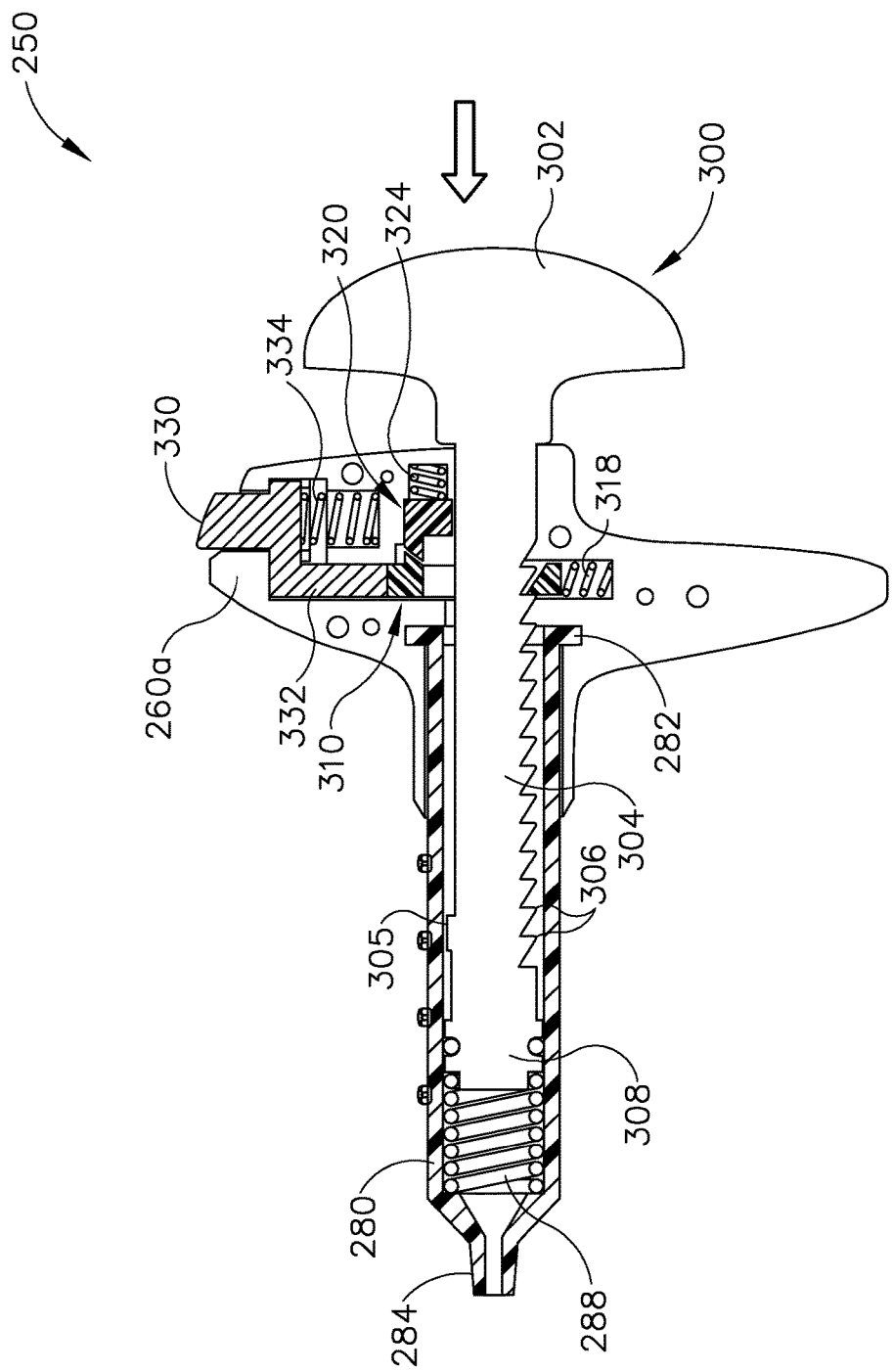
FIG. 10B depicts a cross-sectional side view of the inflator of FIG. 7, with the plunger in a distal position.
Figure 10C:
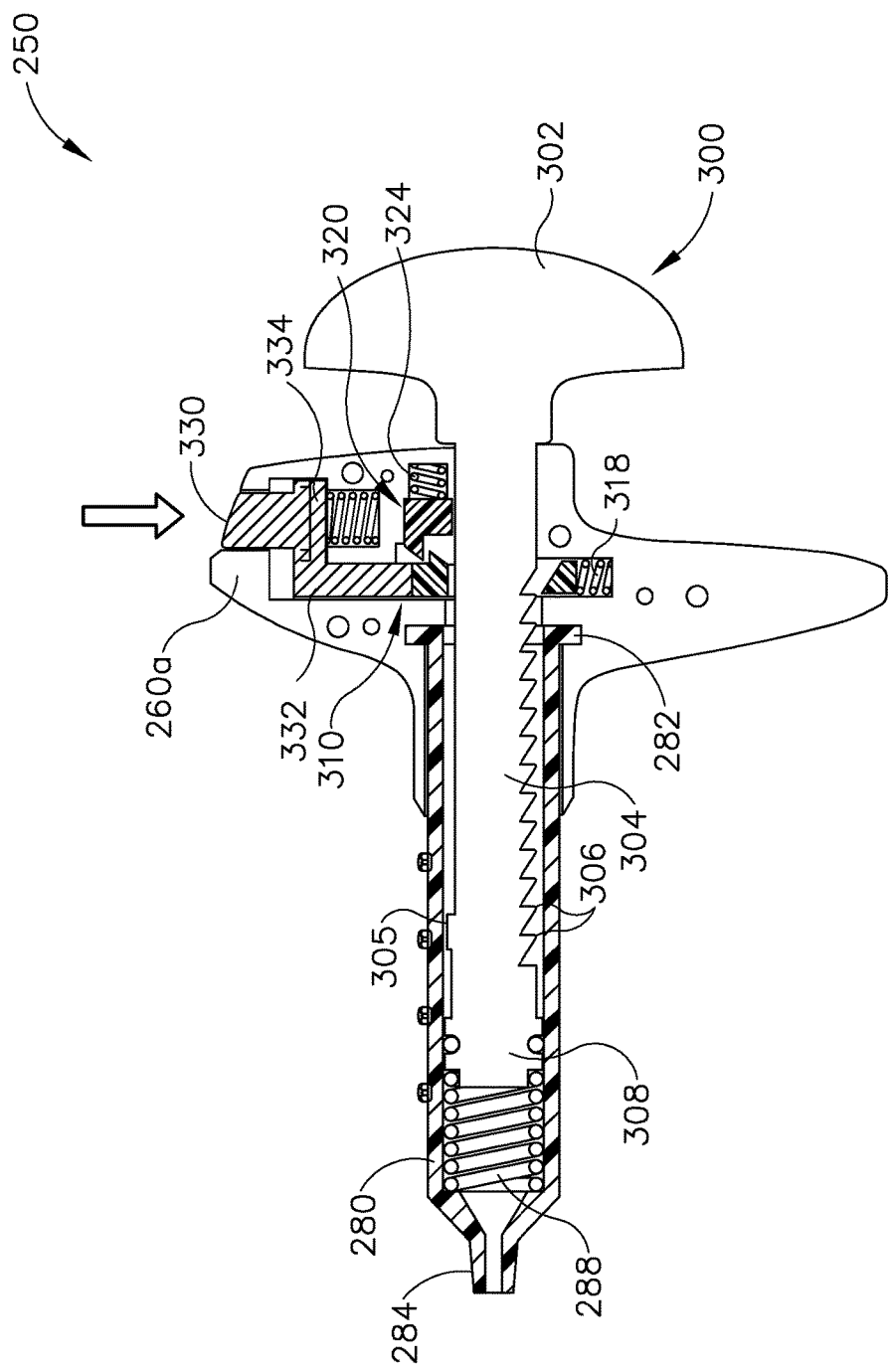
FIG. 10C depicts a cross-sectional side view of the inflator of FIG. 7, with the plunger in a distal position, and with a button actuated to release the ratchet block from the plunger driver.
Figure 10D:
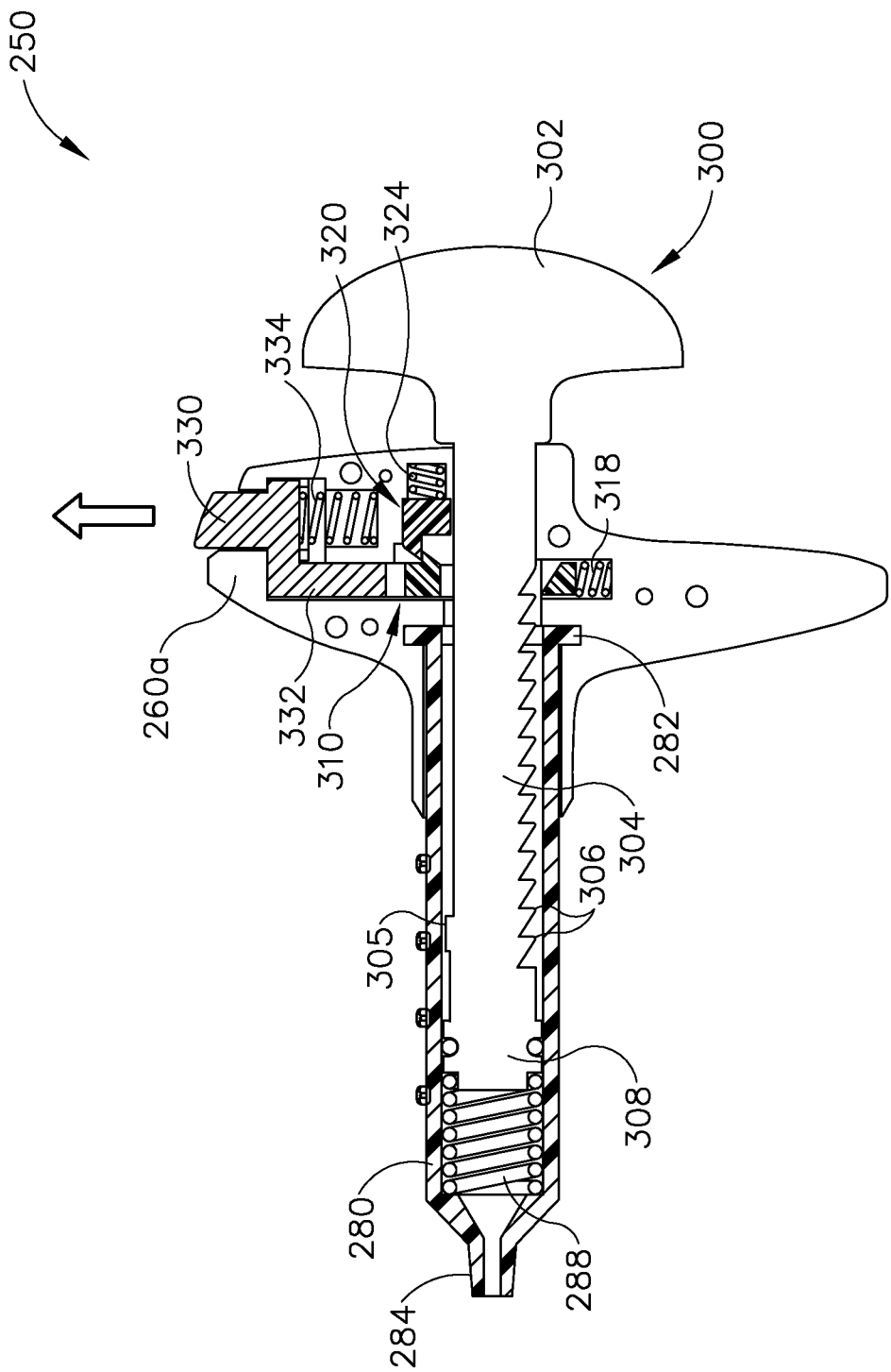
FIG. 10D depicts a cross-sectional side view of the inflator of FIG. 7, with the plunger in a distal position, with the button released, and with a latch holding the ratchet block in a position where the ratchet block remains disengaged from the plunger driver.
Figure 10E:
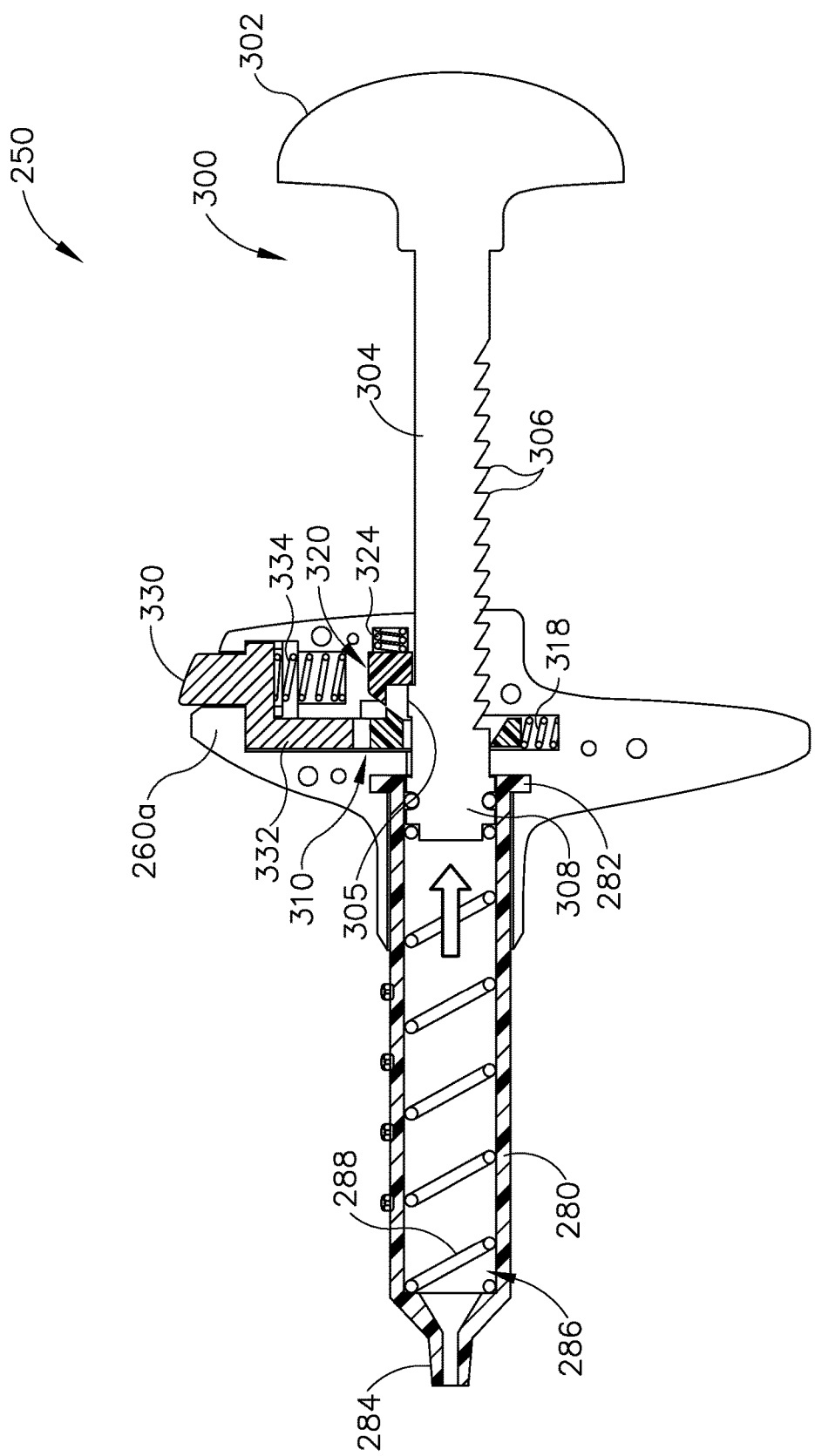
FIG. 10E depicts a cross-sectional side view of the inflator of FIG. 7, with the plunger in a proximal position, and with a latch disengagement feature of the plunger driver disengaging the latch from the ratchet block.
Figure 11:
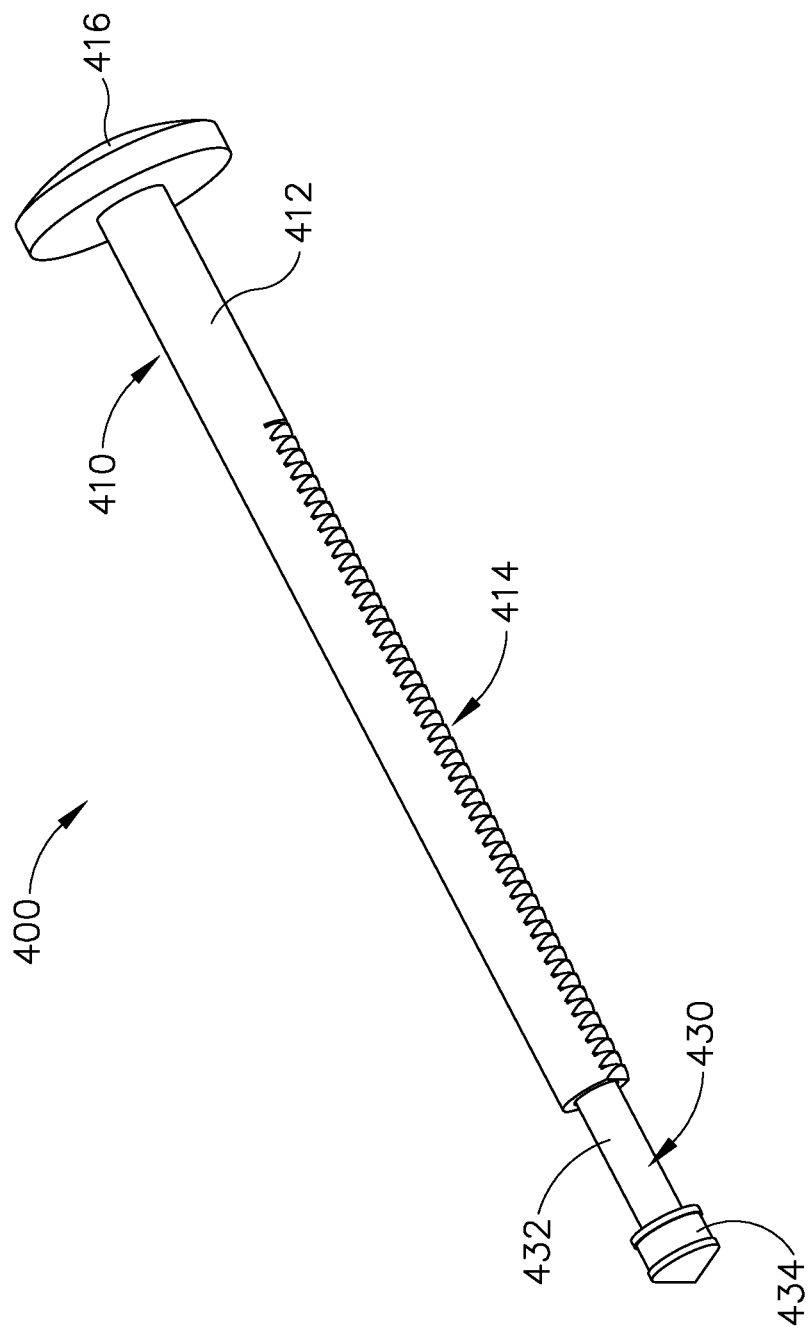
FIG. 11 depicts a perspective view of an exemplary alternative plunger assembly that may be incorporated into the inflator of FIG. 7.
Figure 12:
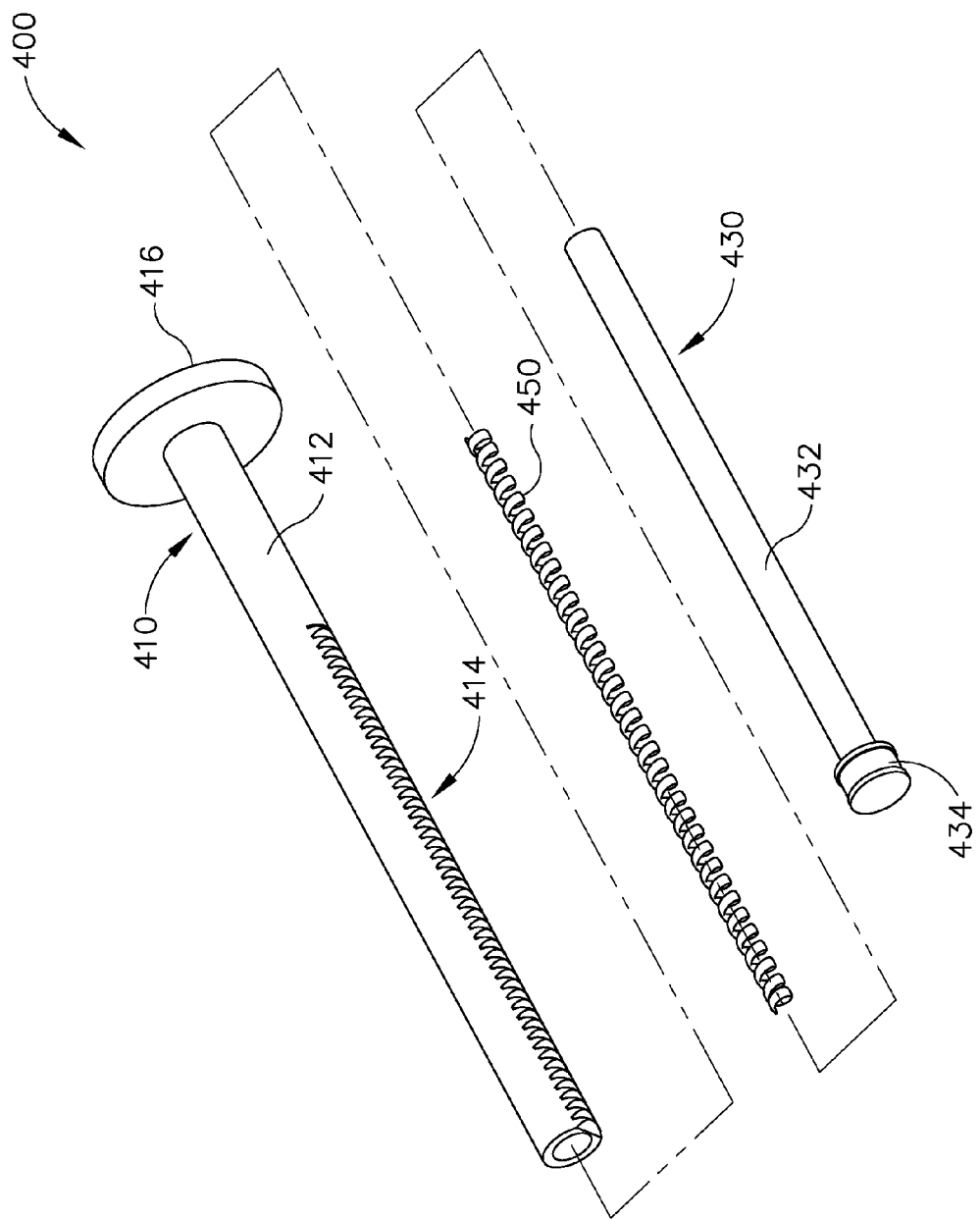
FIG. 12 depicts an exploded view of the plunger assembly of FIG. 11.

When the operator relaxes their grip on grip features (262, 264, 302), spring (288) drives plunger actuator (300) proximally, as shown in the transition from FIG. 10D to FIG. 10E. Once plunger actuator (300) reaches the proximal position shown in FIG. 10E, latch engagement feature (305) drives block latch (320) proximally, which disengages cam feature (322) from upper shelf (317) of cam feature (316). This disengagement of cam feature (316) enables spring (318) to drive ratcheting block (310) upwardly. In some versions, ratcheting block (310) does not actually travel upwardly until the operator advances plunger actuator (300) distally just enough to enable pawl feature (314) to seat within a valley preceding the first sawtooth (306), as shown in FIG. 10A. The above components may be configured such that block latch (320) does not travel distally (under the influence of spring (324)) enough to engage ratcheting block (310) until ratcheting block has first traveled upwardly far enough for upper shelf (317) to clear cam feature (322). In other words, block latch (320) does not impede upward movement of ratcheting block (310) during the transition from the arrangement shown in FIG. 10E back to the arrangement shown in FIG. 10A.

In an exemplary use of inflator (250), a operator may start with plunger actuator (300) advanced to a distal position as shown in FIG. 10B. The operator may then position port (284) in a bowl or other container of saline to draw fluid from. In instances where port (284) is coupled with one end of flexible tube (46), the operator may position the other end of flexible tube (46) in the saline. In either case, the operator may then depress pushbutton (330) to disengage ratcheting block (310) from shaft (340) as shown in FIG. 10C. While maintaining a grip on grip features (262, 264, 302), the operator may release pushbutton (330) as shown in FIG. 10D. Next, the operator may relax their grip on grip features (262, 264, 302), allowing spring (288) to drive plunger actuator (300) proximally toward the position shown in FIG. 10E. This will in turn translate piston (308) proximally within syringe barrel (280), thereby drawing the saline (or other fluid) into reservoir (286). The operator may then remove port (284) or flexible tube (46) from the saline container.

At this stage, the operator may advance plunger actuator (300) distally in order to purge air from reservoir (286). For instance, the operator may orient inflator (250) such that port (284) is positioned upwardly to gather air at the top of reservoir (286) before squeezing on grip features (262, 264, 302) to advance plunger actuator (300) distally in order to purge air from reservoir (286). As the operator advances plunger actuator (300) distally, pawl feature (314) will ratchet along sawteeth (306) to prevent plunger actuator (300) from retracting proximally if and when the operator relaxes their grip on grip features (262, 264, 302).

Once reservoir (286) has been sufficiently filled with fluid and air has been purged, the operator may couple inflator (250) with dilation catheter (20), such as by coupling port (284) with lateral port (26) via a flexible tube (46). In some instances, a conventional fluid pressure gauge (not shown) may be coupled in the fluid path between port (284) and lateral port (26) (e.g., via a "T" fitting, etc.). Of course, inflator (250) may alternatively include an integral pressure gauge. With dilator (22) being suitably positioned within an anatomical passageway (e.g., an ostium (O), etc.), the operator may then advance plunger actuator (300) distally relative to housing (260) to advance piston (308) within syringe barrel (280), thereby transferring fluid from reservoir (286) to dilator (22). The operator may observe the pressure reading at the pressure gauge while advancing plunger actuator (300) distally in order to determine when the appropriate fluid pressure level has been reached. Again, pawl feature (314) will ratchet along sawteeth (306) as the operator advances plunger actuator (300) distally, to prevent plunger actuator (300) from retracting proximally if and when the operator relaxes their grip on grip features (262, 264, 302).

Once the operator has attained the desired level of pressure in dilator (22) within the anatomical passageway to dilate the anatomical passageway, the operator may pause for an approximate, predetermined period of time (e.g., approximately three seconds, etc.). The operator may then depress pushbutton (330) to once again disengage ratcheting block (310) from sawteeth (306), then relax their grip on grip features (262, 264, 302). This will allow spring (288) to drive plunger actuator (300) proximally, thereby drawing fluid from dilator (22) back into reservoir (286). With dilator (22) now deflated, dilator (22) may be retracted from the patient. Alternatively, if the operator wishes to dilate additional anatomical passageways, dilator (22) may be positioned in the next anatomical passageway, and the operator may repeat the above steps to dilate that next anatomical passageway. Thus, the same volume of fluid within reservoir (286) may be used repeatedly to dilate a plurality of anatomical passageways, without having to withdraw dilator (22) from the patient, and without having to decouple inflator (250) from the rest of dilator catheter system (10), until all of the desired dilations have been completed. Other suitable variations of inflator (250) will be apparent to those of ordinary skill in the art in view of the teachings herein. Similarly, other suitable ways in which inflator (250) may be used will be apparent to those of ordinary skill in the art in view of the teachings herein.

C. Exemplary Alternative Plunger Assembly for Inflator with Ratcheting Drive

Figure 13A:
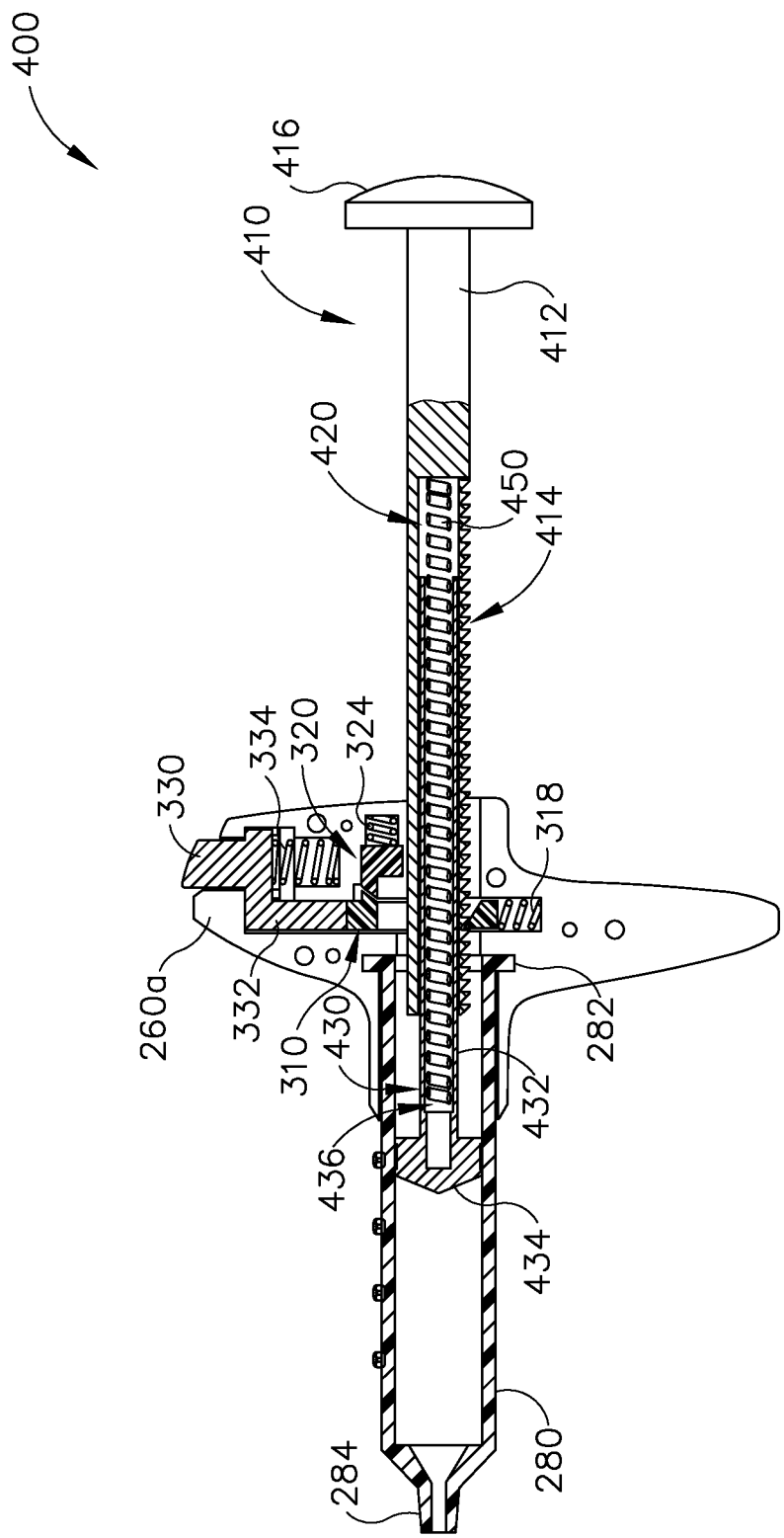
FIG. 13A depicts the plunger assembly of FIG. 11 incorporated into the inflator of FIG. 7, with the plunger assembly in a first stage of actuation.
Figure 13B:
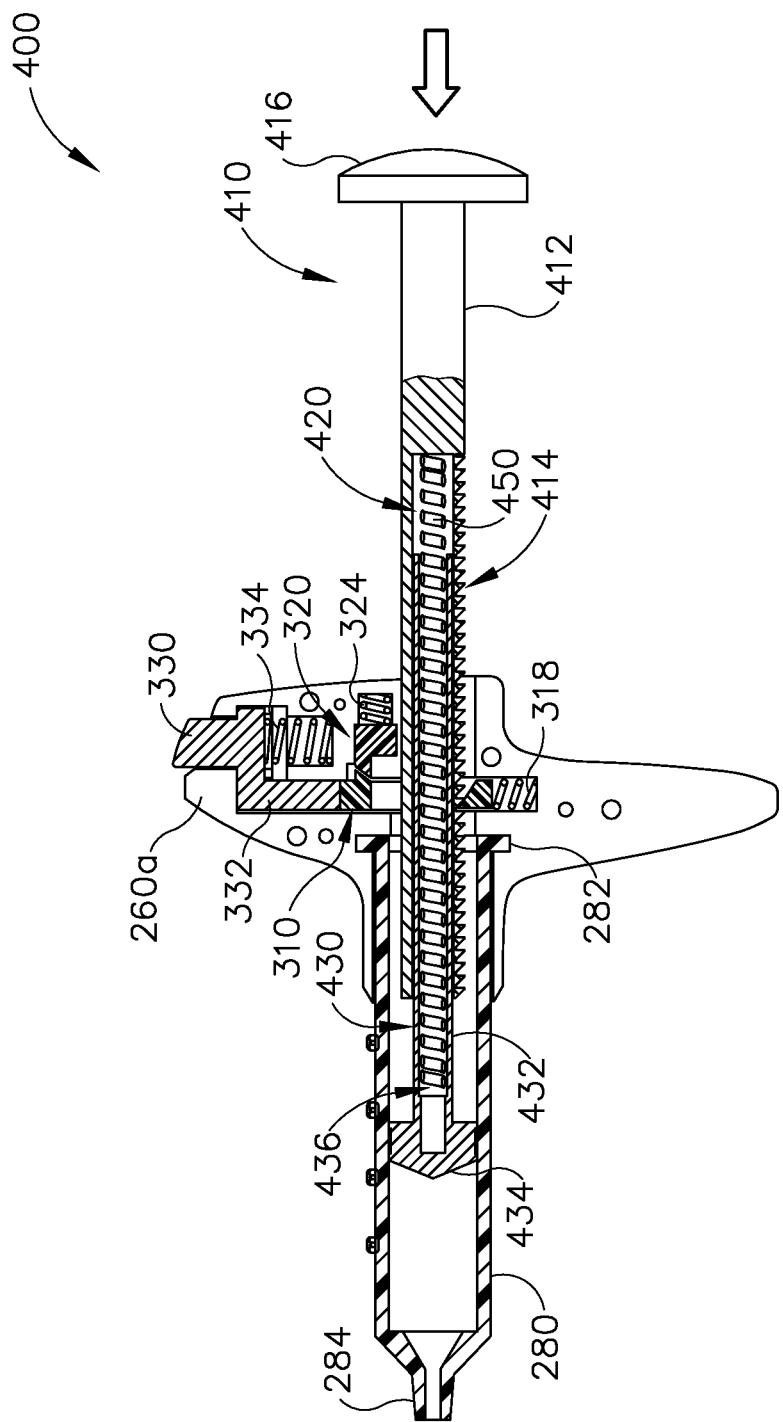
FIG. 13B depicts the plunger assembly of FIG. 11 incorporated into the inflator of FIG. 7, with the plunger assembly in a second stage of actuation.
Figure 13C:
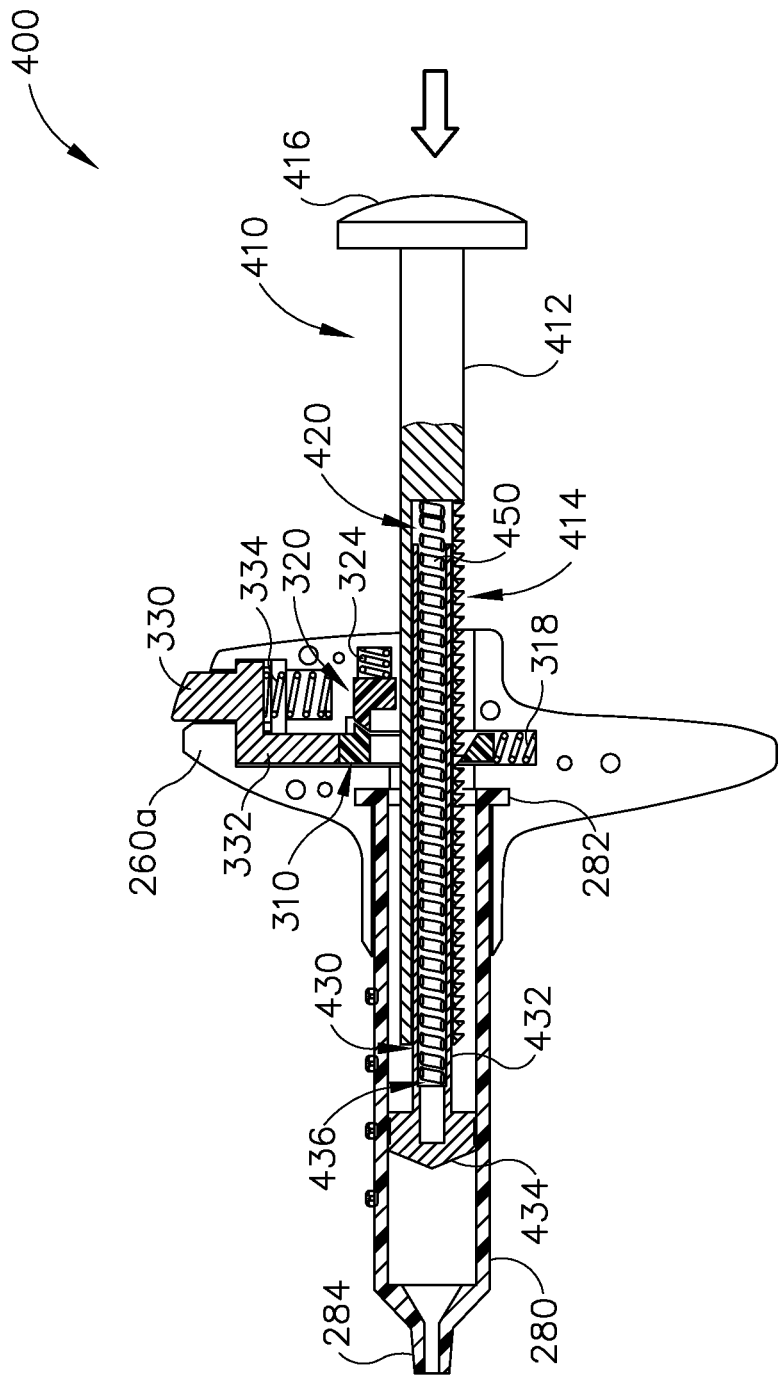
FIG. 13C depicts the plunger assembly of FIG. 11 incorporated into the inflator of FIG. 7, with the plunger assembly in a third stage of actuation.

FIGS. 11-13C show an exemplary alternative plunger assembly (400) that may be readily incorporated into inflator (250) in place of plunger actuator (300). Plunger assembly (400) of this example comprises a drive rod (410), a piston rod (430), and a coil spring (450). Drive rod (410) comprises an elongate shaft (412) with a set of teeth (414) disposed along a portion of the length of shaft (412). Teeth (414) have a sawtooth configuration in the present example, just like sawteeth (306) described above, though it should be understood that any other suitable configuration may be used. A head (416) is located at the proximal end of shaft (412). Piston rod (430) comprises a shaft (432) and a piston head (434) located at the distal end of shaft (432). As best seen in FIGS. 13A-13C, shafts (412, 432) each define respective bores (420, 436). Coil spring (450) is coaxially disposed in bores (420, 436). Shaft (432) is also slidably disposed in bore (420). Coil spring (450) provides a distal bias to piston rod (430) relative to drive rod (410) while still allowing piston rod (430) to be disposed in bore (420) of drive rod (410).

As also shown in FIGS. 13A-13C, plunger assembly (400) configured to engage housing (260) and syringe barrel (280) such that piston head (434) is disposed in syringe barrel (280); and such that teeth (414) engage ratcheting block (310). As described above with respect to plunger actuator (300), plunger assembly (400) may be advanced distally from the position shown in FIG. 13A to the positions shown in FIGS. 13B and 13C to drive fluid from syringe barrel (280), to thereby selectively inflate dilator (22). During this advancement, ratcheting block (310) ratchets against teeth (414). Thus, if the operator were to stop pressing distally on head (416), ratcheting block (310) would engage teeth (414) to prevent plunger assembly (400) from moving proximally, despite a proximally directed bias from a spring (not shown) positioned in syringe barrel (280). Plunger assembly (400) would thus maintain its longitudinal position relative to housing (260) and also maintain its position after reaching the stages shown in FIGS. 13B and 13C, until the operator depresses pushbutton (330).

In the present example, coil spring (450) regulates the response of piston rod (430) to distal advancement of drive rod (410) based on the pressure of fluid contained within the fluid circuit of dilation catheter system (10). In the transition from the state shown in FIG. 13A to the state shown in FIG. 13B, the fluid pressure has increased slightly. This has caused coil spring (450) to not compress significantly, such that piston rod (430) has translated distally at approximately the same rate as drive rod (410). However, in the transition from the state shown in FIG. 13B to the state shown in FIG. 13C, the fluid pressure has increased significantly. This has caused coil spring (450) to compress significantly, such that piston rod (430) has translated distally at a significantly lower rate than drive rod (410). In other words, as the fluid pressure within dilation catheter system (10) increases, the responsiveness of piston rod (430) to distal advancement of drive rod (410) decreases. In some instances, plunger assembly (400) may reach a point (e.g., fluid pressure at 12 atmospheres) where piston rod (430) stops moving distally in response to distal advancement of drive rod (410), such that coil spring (450) just continues to compress. The fluid pressure response from advancement of plunger assembly (400) may thus eventually flatten out due to compression of coil spring (450).

The operator may understand that the fluid pressure in dilation catheter system (10) has reached an appropriate level when the operator is unable to see a further increase in fluid pressure (e.g., as indicated by a pressure gauge, etc.) despite continued advancement of drive rod (410). Plunger assembly (400) may thus provide additional user feedback relating to fluid pressure, in addition to effectively restricting the amount of fluid pressure that plunger assembly (400) may generate. In some instances, drive rod (410) also includes a feature that is configured to ground out on housing (460), such that housing (460) will restrict distal translation of drive rod (410). By way of example only, such a grounding feature may serve as a hard stop to prevent drive rod (410) from reaching a point where the proximal end of piston rod (430) reaches the proximal end of bore (420) in drive rod (410).

It should also be understood that the spring constant of coil spring (450) may be selected to provide compression of coil spring (450) in response to the fluid pressure reaching a certain value. In other words, the fluid pressures that may be achieved using plunger assembly (400) may vary based on the spring constant of coil spring (450). Plunger assembly (400) may also be configured to be adjustable, such that plunger assembly (400) may be selectively adjustable to achieve a particular fluid pressure. While plunger assembly (400) of the present example includes a coil spring (450) to provide an elastic coupling between drive rod (410) and piston rod (430), it should be understood that any other suitable resilient member(s) and/or other feature(s) may be used to provide an elastic coupling between drive rod (410) and piston rod (430). By way of example only, a dilation catheter system (10) may be modified to include an elastic expansion chamber that is in series or in parallel with the fluid circuit of dilation catheter system (10). Other suitable alternatives will be apparent to those of ordinary skill in the art in view of the teachings herein.

While the foregoing example includes plunger assembly (400) as part of inflator (250), it should be understood that plunger assembly (400) may instead be included in various other kinds of inflators. By way of example only, plunger assembly (400) may be used with a conventional syringe barrel and/or with some other conventional component(s). As another merely illustrative example, plunger assembly (400) may be incorporated into inflator (150) in place of plunger (167). Drive rod (410) may thus include a helical threading instead of teeth (414), such that plunger assembly (400) advances linearly in response to rotation of drive rod (410). Other suitable components that may be combined with plunger assembly (400) to selectively inflate dilator (22) will be apparent to those of ordinary skill in the art in view of the teachings herein. Similarly, various modifications that may be made to plunger assembly (400) in order to enable plunger assembly (400) to be combined with various kinds of inflator components will be apparent to those of ordinary skill in the art in view of the teachings herein.

D. Exemplary Inflator System with Pressure Regulator

Figure 14:
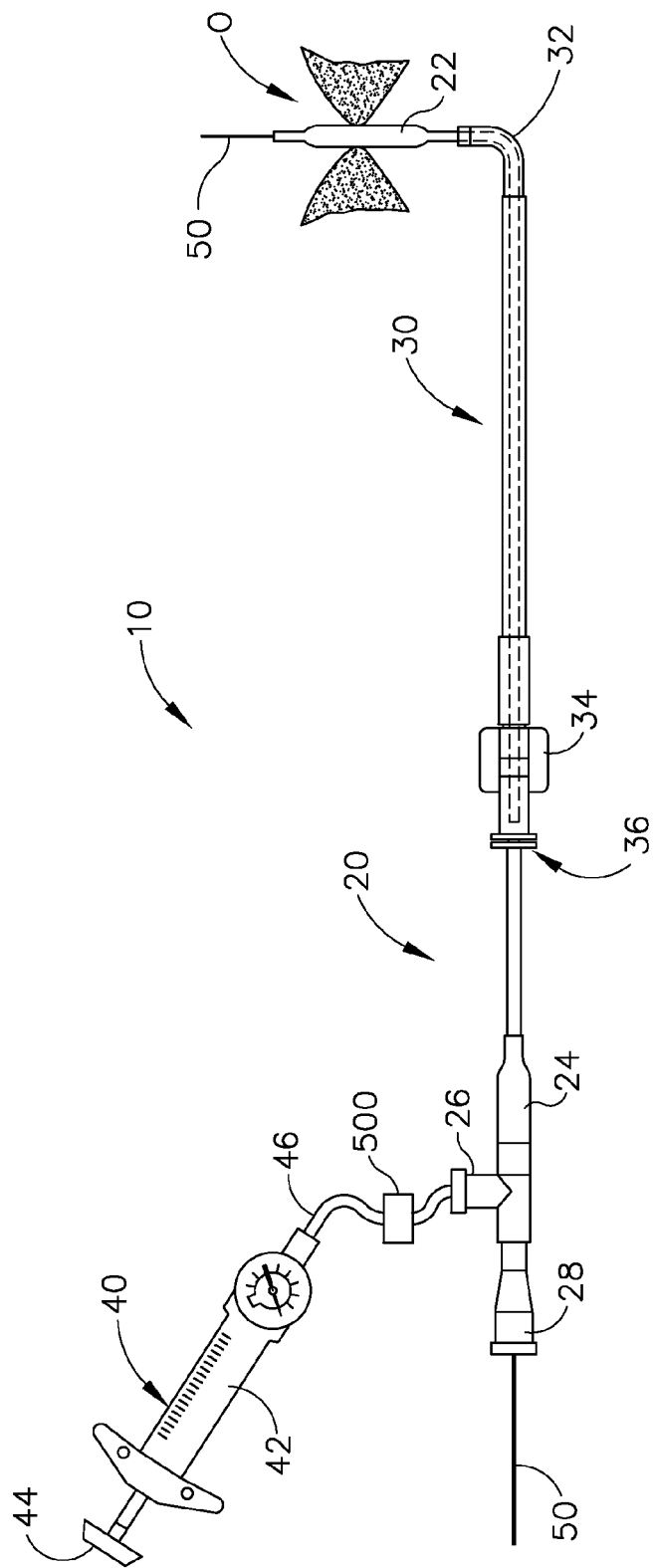
FIG. 14 depicts a side elevational view of an exemplary alternative dilation catheter system.
Figure 15:
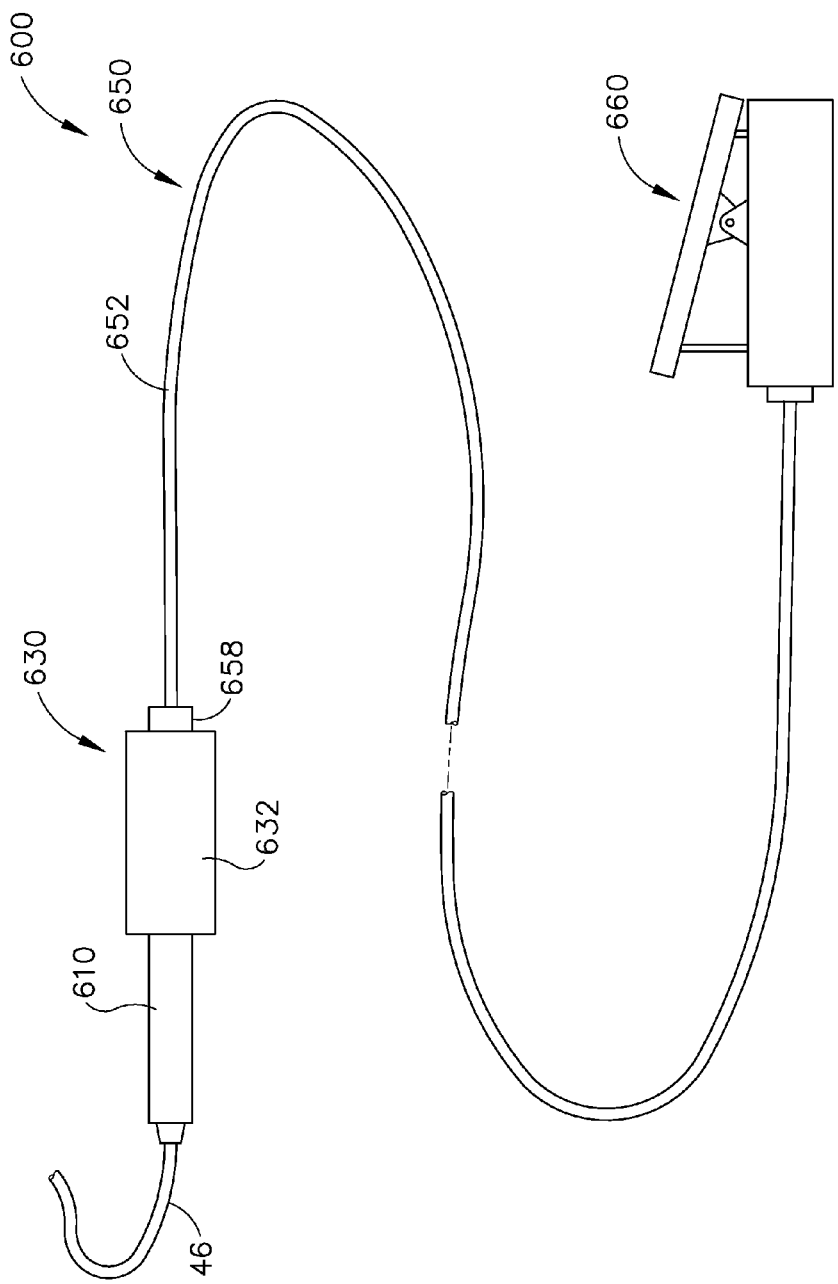
FIG. 15 depicts a side elevational view of an exemplary alternative inflator system suited for use with the dilator catheter system of FIG. 1.

FIG. 14 shows a version of dilator catheter system (10) where a fluid pressure regulator (500) is placed in line between inflator (40) and port (26) of dilation catheter (20). Fluid pressure regulator (500) is coupled directly with tube (46), such that fluid from inflator (40) and tube (46) must pass through fluid pressure regulator (500) in order to reach port (26) of dilation catheter (20). Fluid pressure regulator (500) is operable to restrict the fluid pressure that inflator (40) is operable to achieve in dilator catheter system (10). For instance, fluid pressure regulator (500) may act as a fuse switch that closes the fluid path between tube (46) and port (26) of dilation catheter (20) in response to the fluid pressure reaching a predetermined value. In some versions, fluid pressure regulator (500) is adjustable such that the operator may select a fluid pressure value that will trigger fluid pressure regulator (500) to close the fluid path between tube (46) and port (26) of dilation catheter (20). In some other versions, fluid pressure regulator (500) comprises a frangible diaphragm and/or some other frangible component(s). In still other versions, fluid pressure regulator (500) comprises a conventional spring-loaded pressure relief valve. In some such versions, fluid pressure regulator (500) diverts fluid to a reservoir or other chamber when the operator continues to actuate inflator (40) after the fluid pressure reaches a certain level, such that the diversion of fluid prevents the fluid pressure from increasing further. Various suitable forms that fluid pressure regulator (500) may take will be apparent to those of ordinary skill in the art in view of the teachings herein.

E. Exemplary Foot-Driven Assembly for Inflator

FIGS. 15-19 show another exemplary inflator system (600) that may be readily incorporated into dilator catheter system (10) in place of inflator (40). Inflator system (600) of this example comprises an adapter assembly (630), a cable assembly (650), and a pedal assembly (660). As will be described in greater detail below, adapter assembly (630) is operable to couple with syringe components to selectively drive fluid through tube (46). As will also be described in greater detail below, pedal assembly (660) is coupled with adapter assembly (630) via cable assembly (650) such that pedal assembly (660) is operable to drive adapter assembly (630) via cable assembly (650). By relying on actuation of pedal assembly (660) by an operator's foot, inflator system (600) may be less reliant on the hand strength of the operator than other inflator systems. In other words, inflator system (600) of this example may be particularly suited for operators having relatively small or weak hands.

Figure 16:
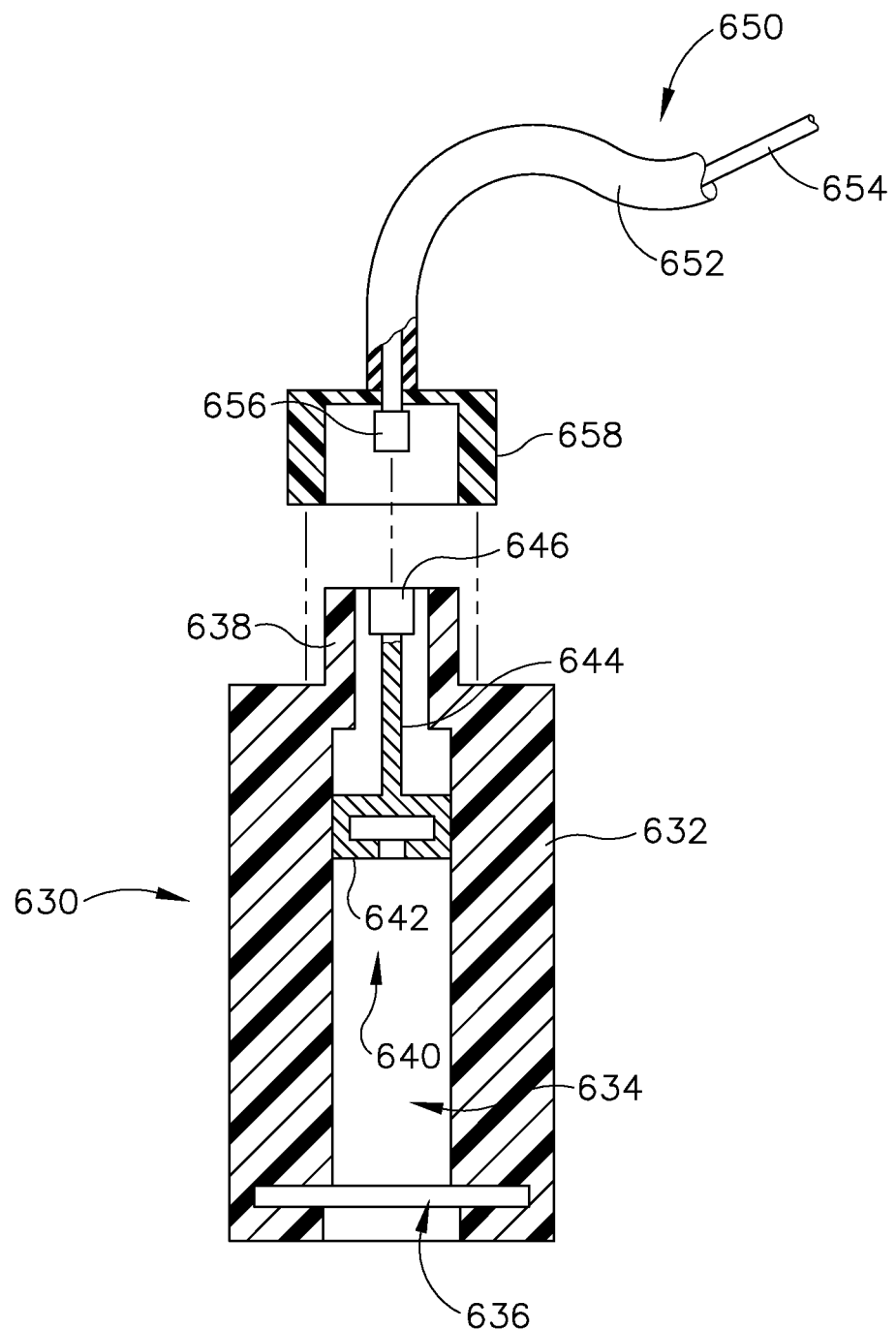
FIG. 16 depicts a side cross-sectional view of an inflator adapter of the inflator system of FIG. 15.

As shown in FIG. 16, adapter assembly (630) of the present example comprises a body (632) that defines a bore (634) and an annular recess (636). The upper end of body (632) also includes a coupling feature (638). A plunger driver (640) is slidably disposed in bore (634). The lower end of plunger driver (640) includes a plunger coupling feature (642) while the upper end of plunger driver (640) includes a cable coupling feature (646). A rigid stem (644) extends between coupling features (641, 646).

As also shown in FIG. 16, cable assembly (650) of the present example comprises an outer sheath (652) and a drive cable (654). A coupling feature (658) is secured to the distal end of outer sheath (652). Coupling feature (658) of cable assembly (650) is configured to mate with coupling feature (638) of body (632) to thereby selectively couple cable assembly (650) with adapter assembly (630). By way of example only, coupling features (658, 638) may be configured to couple together in a threaded fashion, in a snap fit fashion, in a bayonet fashion, and/or in any other suitable fashion. Various suitable ways in which coupling features (658, 638) may be configured and operable will be apparent to those of ordinary skill in the art in view of the teachings herein. Outer sheath (652) is laterally flexible in this example, though outer sheath (652) has sufficient column strength to provide a mechanical ground between pedal assembly (660) and coupling feature (658) (and, hence, body (632)).

Drive cable (654) is configured to translate longitudinally within outer sheath (652). While drive cable (654) is flexible in this example, drive cable (654) has sufficient column strength to transfer longitudinal forces, such that drive cable (654) is operable to drive plunger driver (640) as will be described in greater detail below. By way of example only, drive cable (654) may comprise a conventional push/pull cable. A cable coupling feature (656) is secured to the distal end of drive cable (654). Cable coupling feature (656) is configured to mate with cable coupling feature (646) of plunger driver (640) to thereby selectively couple drive cable (654) with plunger driver (640). By way of example only, cable coupling features (656, 646) may be configured to couple together in a threaded fashion, in a snap fit fashion, in a bayonet fashion, and/or in any other suitable fashion. Various suitable ways in which cable coupling features (656, 646) may be configured and operable will be apparent to those of ordinary skill in the art in view of the teachings herein.

Figure 17A:
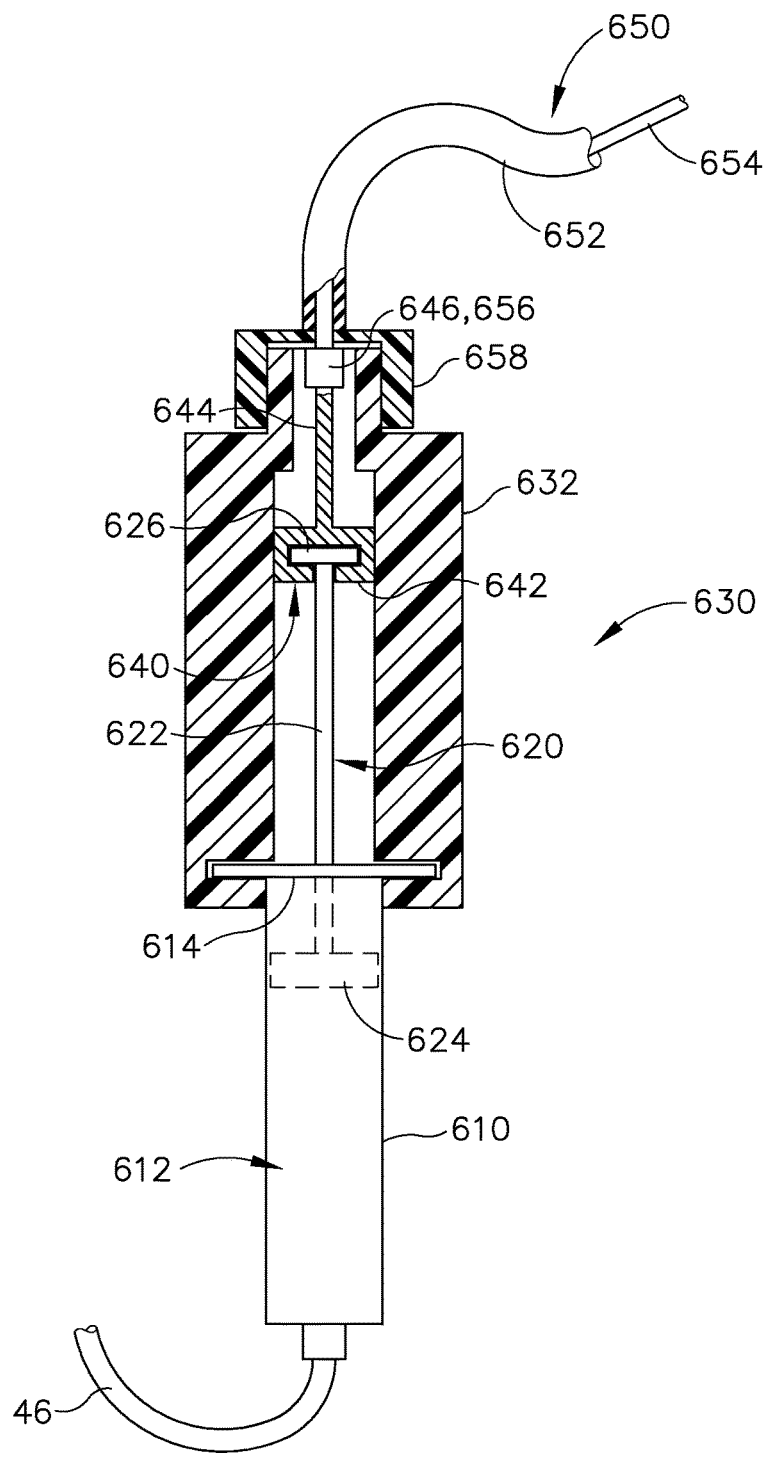
FIG. 17A depicts the inflator adapter of FIG. 16 coupled with a syringe assembly, with the inflator adapter in a non-actuated state.
Figure 17B:
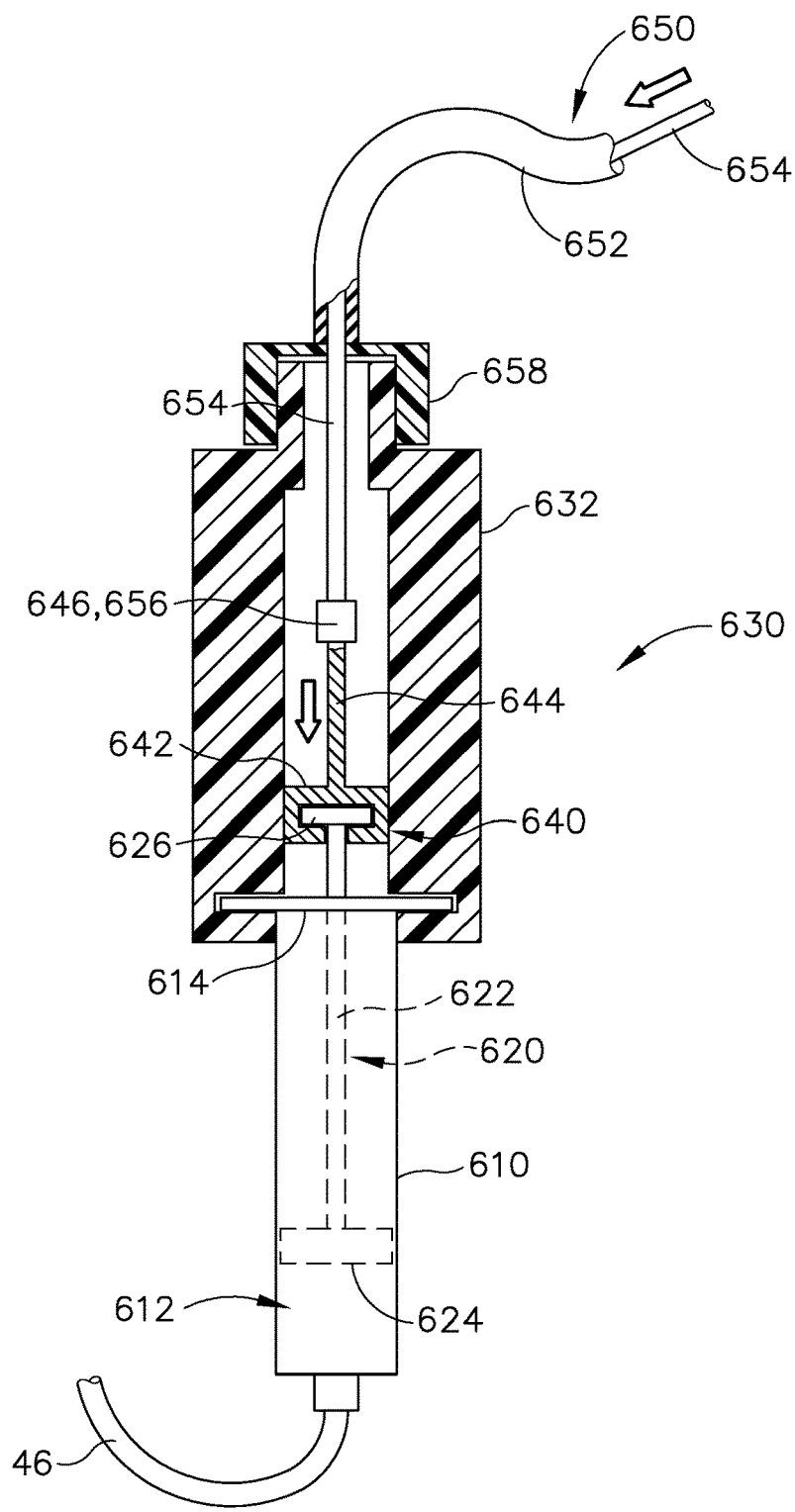
FIG. 17B depicts the inflator adapter of FIG. 16 coupled with a syringe assembly, with the inflator adapter in an actuated state.

As shown in FIGS. 17A-17B, adapter assembly (630) is configured to couple with a conventional syringe assembly that is formed by a syringe barrel (610) and a plunger (620). In particular, syringe barrel (610) includes a flange (614) that is received in annular recess (636) of body (632), thereby coupling syringe barrel (610) with body (632). Plunger (620) includes a stem (622) with a piston head (624) at one end and a push head (626) at the other end. Piston head (624) is slidably disposed in syringe barrel (610) and is operable to selectively vary the volume of a reservoir (612) defined by piston head (624) and syringe barrel (610), by translating within syringe barrel (610). Push head (626) is coupled with plunger coupling feature (642) of plunger driver (640) such that plunger (620) and plunger driver (640) translate unitarily within bore (634) of body (632). Various suitable ways in which plunger coupling feature (642) may couple with push head (626) will be apparent to those of ordinary skill in the art in view of the teachings herein. Similarly, various suitable ways in which flange (614) may couple with annular recess (636) will be apparent to those of ordinary skill in the art in view of the teachings herein.

As seen in the transition from FIG. 17A to FIG. 17B, drive cable (654) is operable to advance relative to outer sheath (652) to drive plunger (620) into syringe barrel (610). Outer sheath (652), coupling feature (658), body (632), and syringe barrel (610) all cooperate to provide a mechanical ground. As plunger (620) is advanced in syringe barrel (610), piston head (624) reduces the volume of reservoir (612), thereby driving fluid from reservoir (612) through tube (46) to inflate dilator (22). It should be understood that drive cable (654) may then be pulled proximally to pull plunger (620) proximally relative to syringe barrel (610), thereby drawing fluid back into reservoir (612) to deflate dilator (22). A merely illustrative example of an assembly that may be used to actuate drive cable (654) distally and proximally will be described in greater detail below. However, it should be understood that any other suitable kind of assembly may be used to actuate drive cable (654), as will be apparent to those of ordinary skill in the art in view of the teachings herein. It should also be understood that the conventional syringe barrel (610) and plunger (620) of the present example are merely illustrative examples. Adapter (630) may be modified to cooperate with various other kinds of inflator devices; and may include an integral functional equivalent of syringe barrel (610) and/or plunger (620).

Figure 18A:
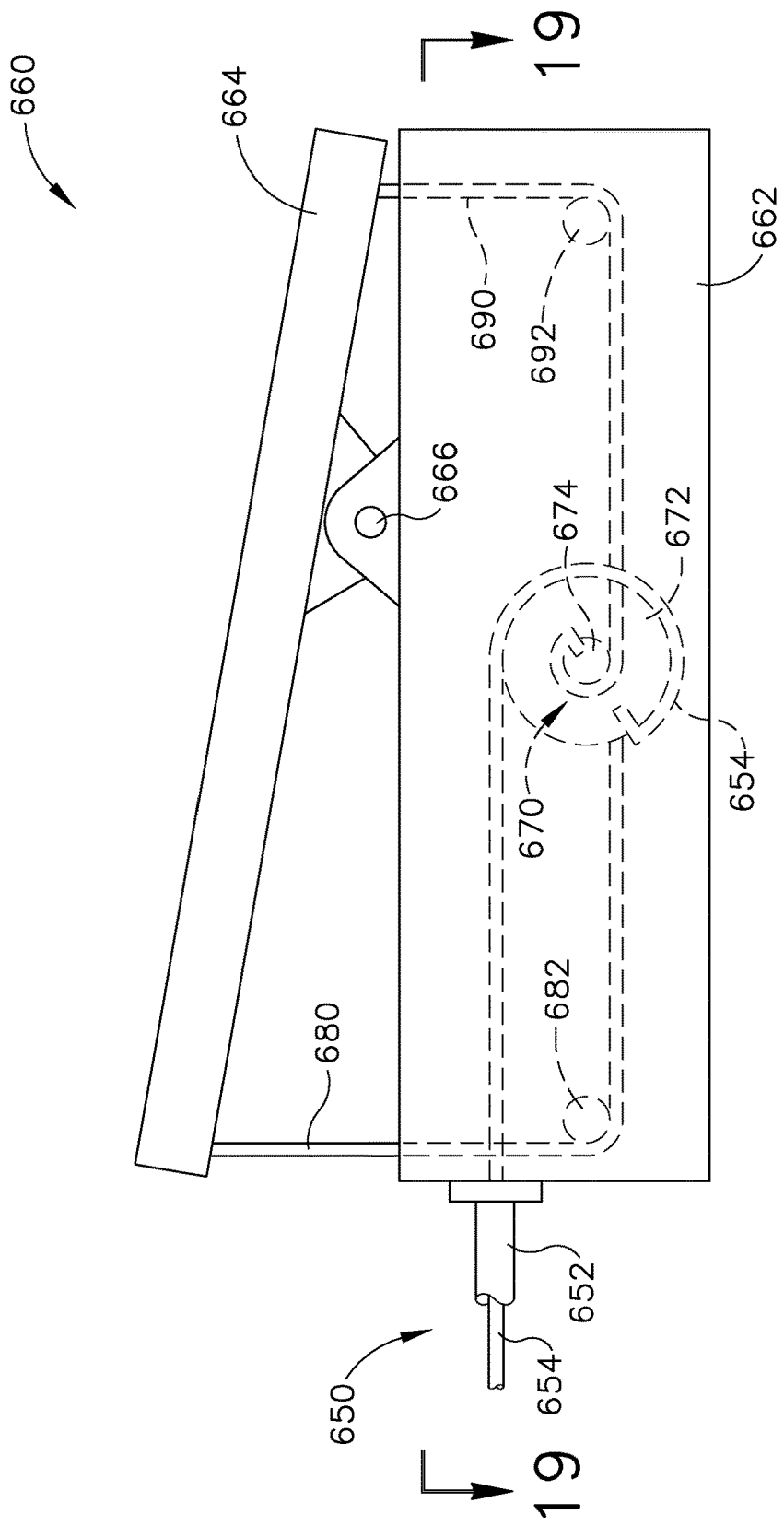
FIG. 18A depicts a side elevational view of a pedal assembly of the inflator system of FIG. 15, with the pedal assembly in a non-actuated state.
Figure 18B:
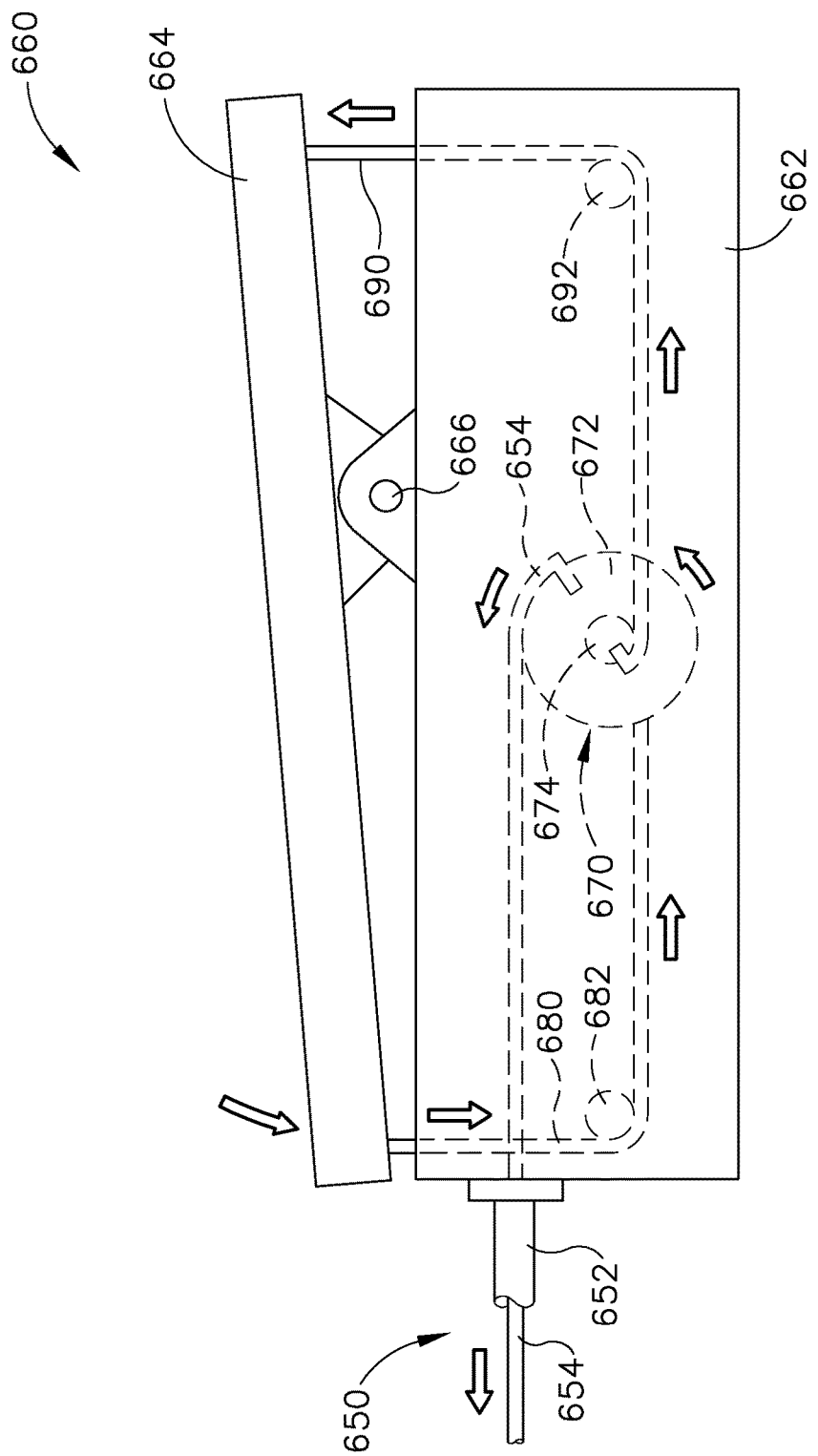
FIG. 18B depicts a side elevational view of the pedal assembly of FIG. 18A, with the pedal assembly driven to an actuated state.
Figure 18C:
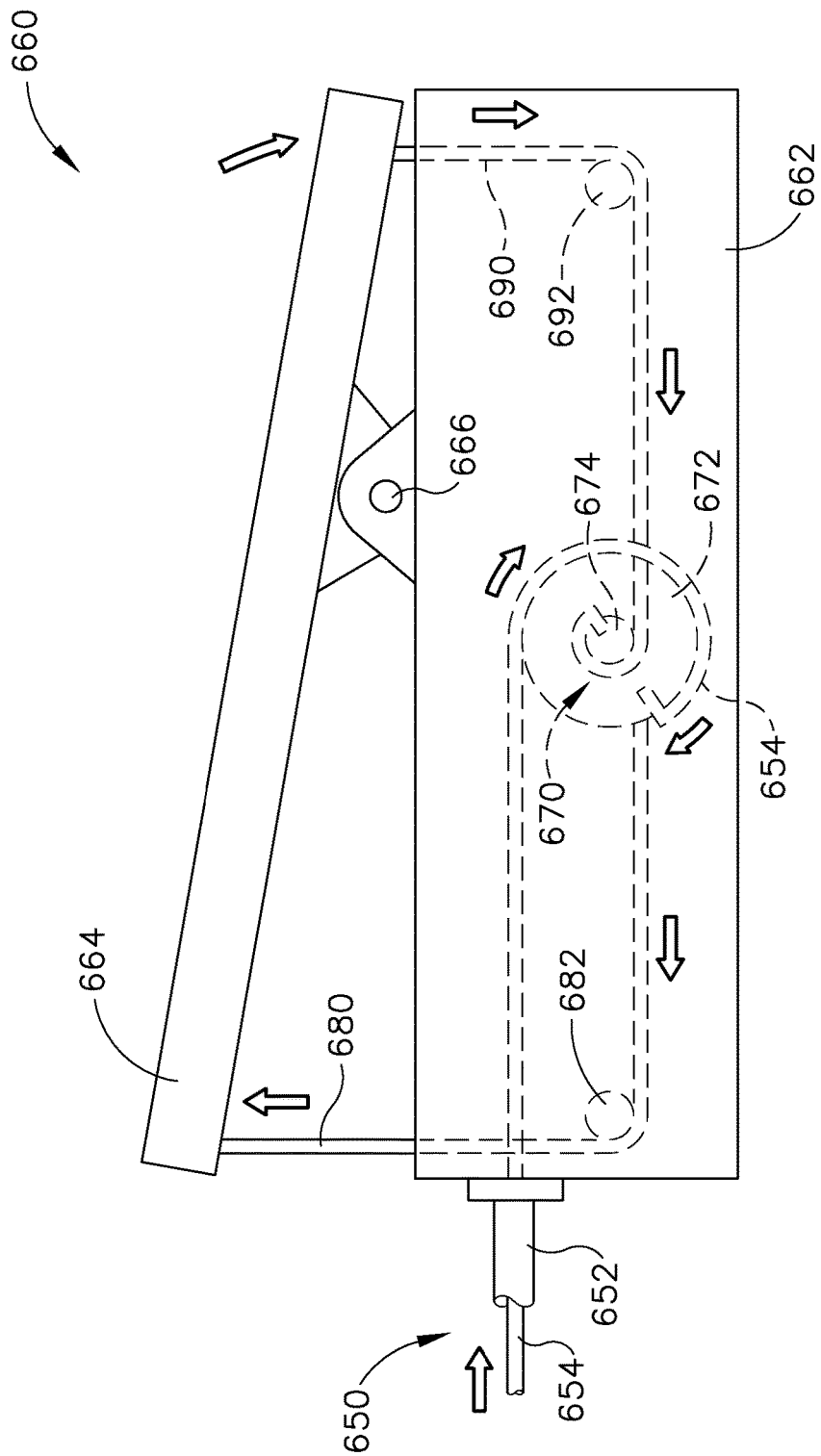
FIG. 18C depicts a side elevational view of the pedal assembly of FIG. 18A, with the pedal assembly driven back to the non-actuated state.
Figure 19:
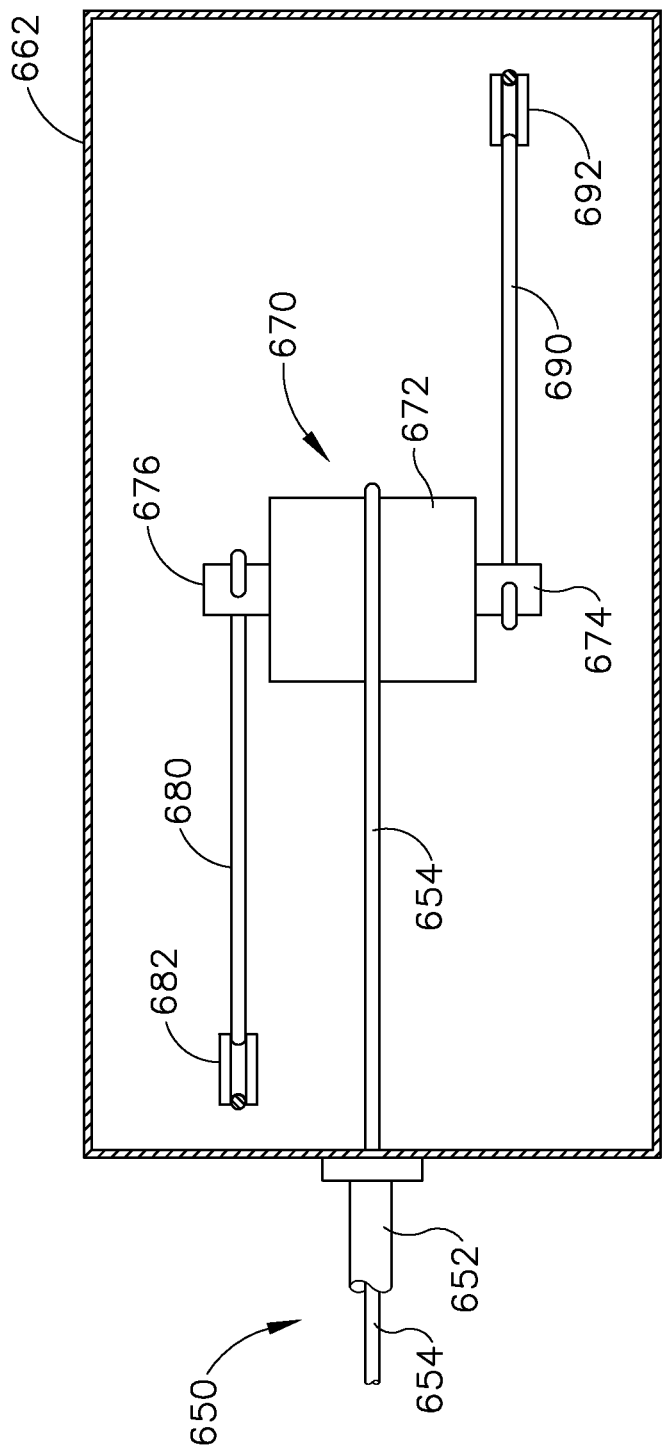
FIG. 19 depicts a top cross-sectional view of the pedal assembly of FIG. 18A, taken along line 19-19 of FIG. 18A.
Figure 20:
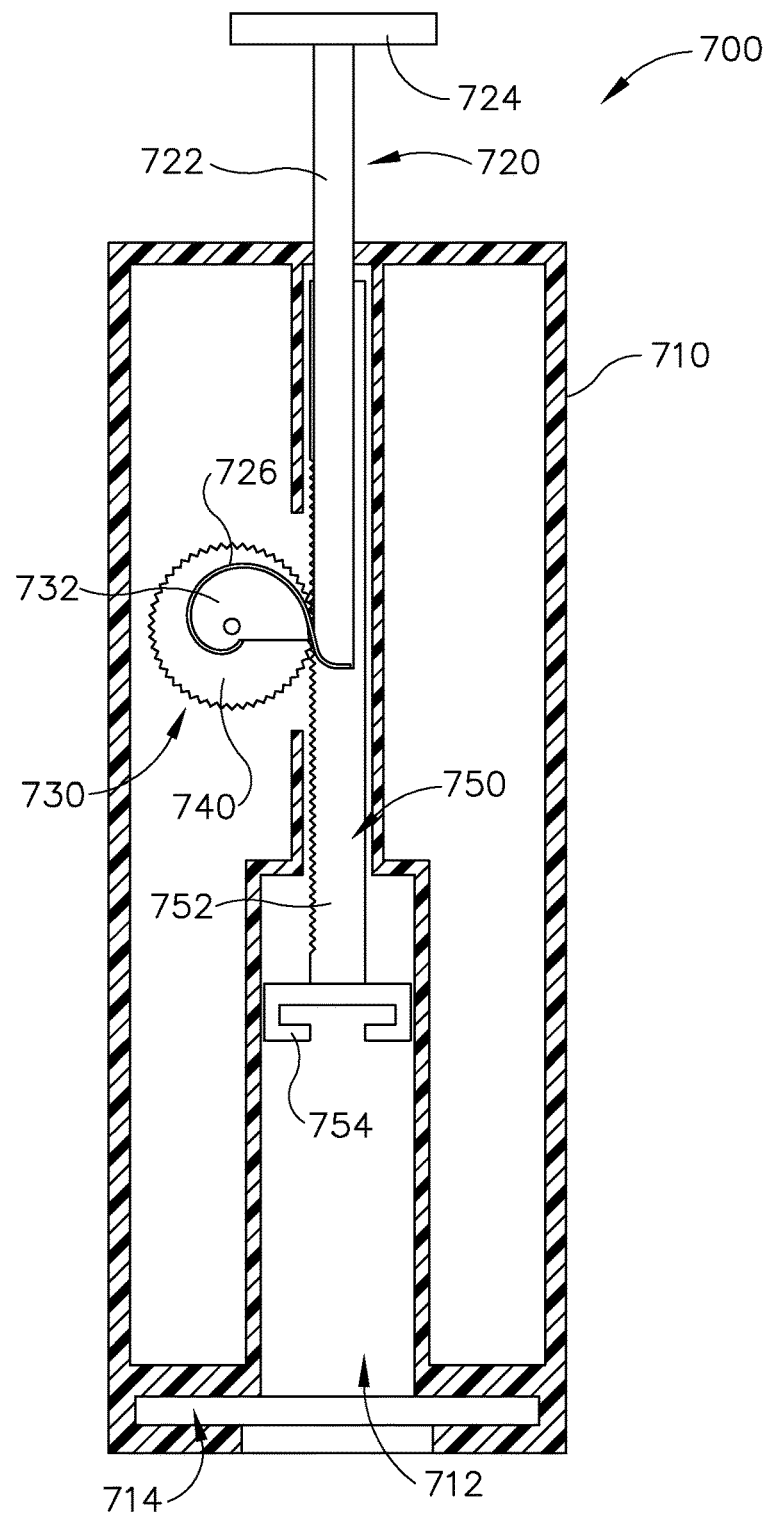
FIG. 20 depicts a side cross-sectional view of another exemplary inflator adapter suited for use with the dilator catheter system of FIG. 1.

FIGS. 18A-19 show pedal assembly (660) in greater detail. Pedal assembly (660) of this example comprises a base (662) and a pedal (664), which is pivotably coupled with base (662) via a pin (666). Pedal (664) is thereby operable to pivotably rock back and forth between the position shown in FIGS. 18A and 18C and the position shown in FIG. 18B. Cable assembly (650) is coupled with pedal assembly (660). In particular, the proximal end of outer sheath (652) is secured to the distal end of base (662). Drive cable (654) extends through base (662) and is secured to a drum (670). In particular, drive cable (654) wraps over the top of the body (672) of drum (670), with a proximal end of drive cable (654) being fixedly secured to body (672) of drum (670). Drum (670) is rotatably supported within base (662) by axles (674, 676), which are best seen in FIG. 19. Axles (674, 676) are coaxially aligned with each other and are coaxially aligned with drum body (672). It should be understood that bushings, bearings, and/or other kinds of features may be used to provide structural support for drum body (672) and axles (674, 676) in base (662) while still permitting drum body (672) and axles (674, 676) to rotate in base (662).

In the present example, pedal (664) is operable to drive drum (670), and thereby actuate drive cable (654), via a pair of pedal cables (680, 690). A first pedal cable (680) is secured to axle (676). In particular, first pedal cable (680) wraps under the bottom of axle (676), with the proximal end of first pedal cable (680) being fixedly secured to axle (676). First pedal cable (680) also wraps along the bottom of a pulley (682), which is rotatably supported in base (662). The distal end of first pedal cable (680) is fixedly secured to the distal portion of pedal (664). Similarly, second pedal cable (690) wraps under the bottom of axle (674), with the distal end of second pedal cable (690) being fixedly secured to axle (674). Second pedal cable (690) also wraps along the bottom of a pulley (692), which is rotatably supported in base (662). The proximal end of second pedal cable (690) is fixedly secured to the proximal portion of pedal (664).

In an exemplary use, pedal assembly (660) starts in the configuration shown in FIG. 18A. At this stage, plunger (620) is in a withdrawn configuration as shown in FIG. 17A, and dilator (22) is in a deflated state. The operator then presses on the distal end pedal (664) using the operator's foot, pivotably driving pedal (664) about pin (666) to the position shown in FIG. 18B. This causes second pedal cable (690) to pull tangentially on axle (674), thereby rotating drum body (672) counterclockwise (when viewed from the perspective shown in FIGS. 18A-18C). This counterclockwise rotation of drum body (672) actuates drive cable (654) distally. It should be understood that pedal assembly (660) may include various guide features that prevent cable (654) from buckling during such distal actuation of drive cable (654). The distal movement of drive cable (654) drives plunger driver (640) and plunger (620) distally, to the position shown in FIG. 17B, thereby inflating dilator (22). As drum body (672) rotates counterclockwise from the position shown in FIG. 18A to the position shown in FIG. 18B, first pedal cable (680) is progressively wrapped about axle (676).

In order to deflate dilator (22), the operator may simply press on the proximal end of pedal (664) using the operator's foot, pivotably driving pedal (664) about pin (666) to the position shown in FIG. 18C. This causes first pedal cable (680) to pull tangentially on axle (676), thereby rotating drum body (672) clockwise (when viewed from the perspective shown in FIGS. 18A-18C). This clockwise rotation of drum body (672) actuates drive cable (654) proximally. The proximal movement of drive cable (654) drives plunger driver (640) and plunger (620) proximally, back to the position shown in FIG. 17A, thereby deflating dilator (22). As drum body (672) rotates clockwise from the position shown in FIG. 18B to the position shown in FIG. 18C, second pedal cable (690) is progressively wrapped about axle (674). The foregoing process of rocking pedal (664) between the position shown in FIGS. 18A and 18C and the position shown in FIG. 18B may be repeated as many times as desired to successively inflate and deflate dilator (22).

It should be understood that pedal assembly (660) may be modified in numerous ways. For instance, the relationship between the diameter of drum body (672) and the diameter of axles (674, 676) may be selected to provide a particular desired ratio between the pivotal displacement of pedal (664) relative to base (662) and the linear displacement of plunger (620) relative to syringe barrel (610). In addition, while drum body (672) and axles (674, 676) all have circular cross-sections in the present example, it should be understood that drum body (672), axle (674), and/or axle (676) may have a non-circular cross-sections in order to provide a ratio of pivotal displacement to linear displacement that varies during the pivotal movement of pedal (664) relative to base. For instance, drum body (672), axle (674), and/or axle (676) may have a teardrop shaped cross-section, an elliptical cross-section, and/or any other suitable kind of non-circular cross-section. Furthermore, regardless of whether the cross-sections are circular or not, drum body (672) and axles (674, 676) may be arranged in an eccentric relationship, such that drum body (672) is not coaxial with axles (674, 676). Such a relationship may also provide a ratio of pivotal displacement to linear displacement that varies during the pivotal movement of pedal (664) relative to base.

Moreover, pedal assembly (660) may be configured such that cables (680, 690) and/or other features are omitted. For instance, in some alternative versions, drum (670) is positioned near the proximal or distal end of base (662) and includes an integral pinion that is engaged with a rack extending downwardly from pedal (664). Such a rack and pinion configuration may provide rotation of drum (670) (and, hence, translation of drive cable (654)) in response to pivoting of pedal (664) relative to base (662). The diameter of the pinion secured to drum body (672) may be selected to provide a desired ratio of pivotal displacement (of drum body (672)) to linear displacement (of drive cable (654)). Alternatively, a transmission assembly (e.g., set of gears) may be used to provide a gear ratio that yields a desired ratio of pivotal displacement (of drum body (672)) to linear displacement (of drive cable (654)). Various other suitable ways in which pedal assembly (660) may be configured will be apparent to those of ordinary skill in the art in view of the teachings herein.

In some instances, pedal assembly (660) and cable assembly (650) are provided as reusable components while adapter assembly (630) is provided as a disposable component. Of course, this is merely optional. In some other instances, adapter assembly (630) is also provided as a reusable component, subject to sterilization.

F. Exemplary Drive Assembly for Inflator with Progressive Mechanical Advantage

Figure 21:
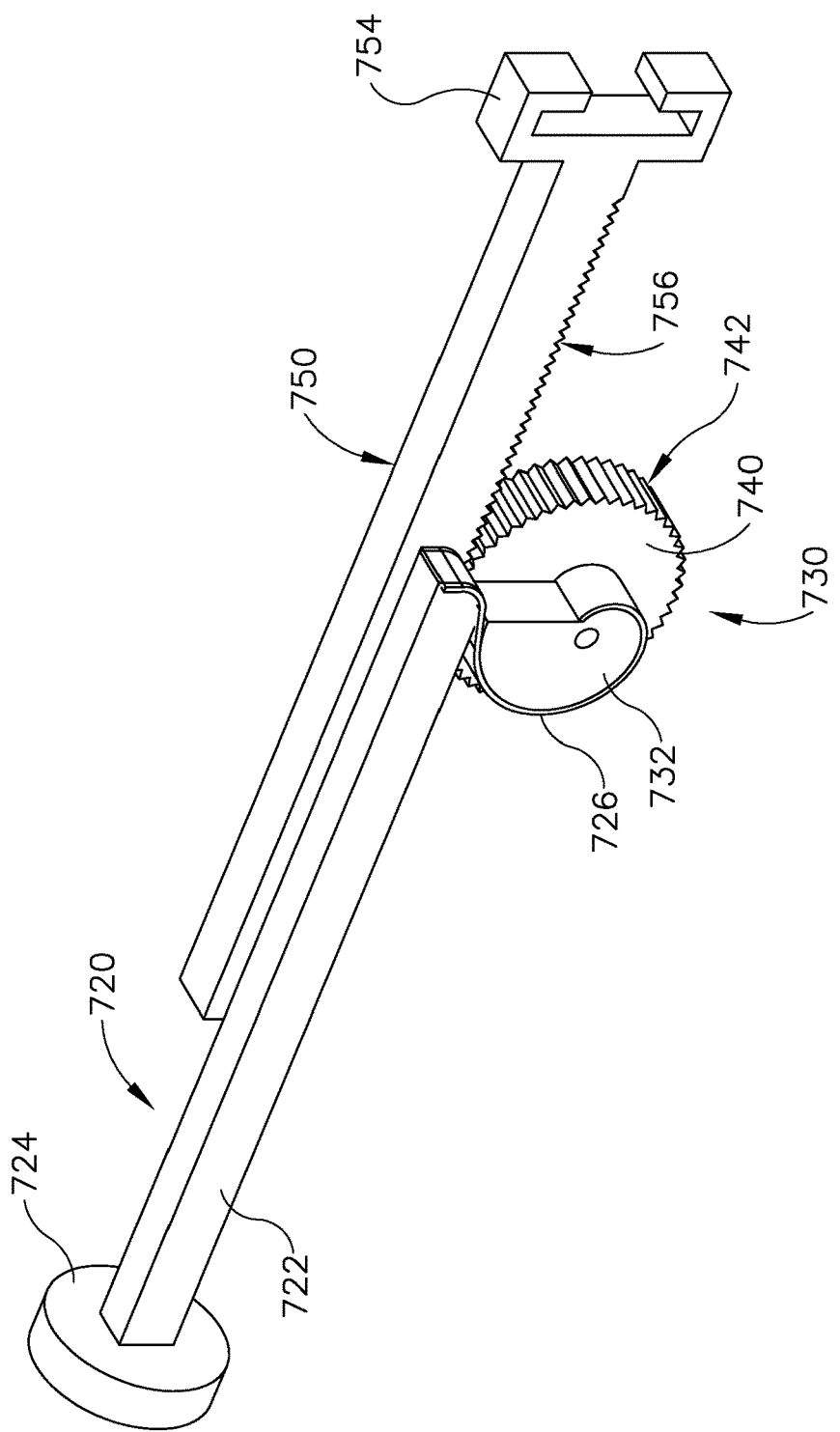
FIG. 21 depicts a perspective view of an actuation assembly of the inflator adapter of FIG. 20.

FIGS. 20-24B show another exemplary inflator assembly (700) that may be readily incorporated into dilation catheter system (10) in place of inflator (40). Inflator assembly (700) of this example comprises a body (710), an actuator (720), a rotary drive member (730), and a plunger driver (750). Body (710) defines a bore (712) and an annular recess (714). As best seen in FIG. 21, actuator (720) includes a shaft (722) and a head (724) located at the proximal end of shaft (722). One end of a band (726) is secured to the distal end of shaft (722). The other end of band (726) is secured to rotary drive member (730). Band (726) is formed of a material that is configured to flex but not stretch. By way of example only, band (726) may be formed of a metal (e.g., a steel ribbon) and/or a polymer.

Figure 22:
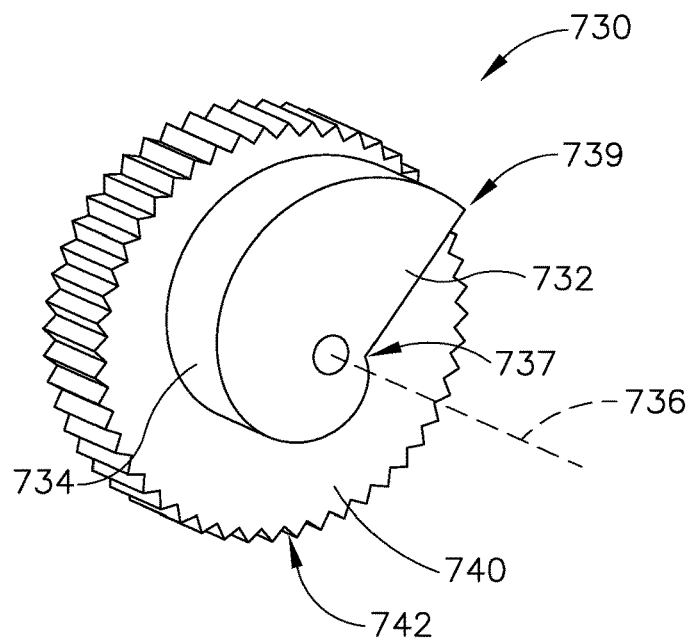
FIG. 22 depicts a perspective view of a rotary drive member of the actuation assembly of FIG. 21.
Figure 23:
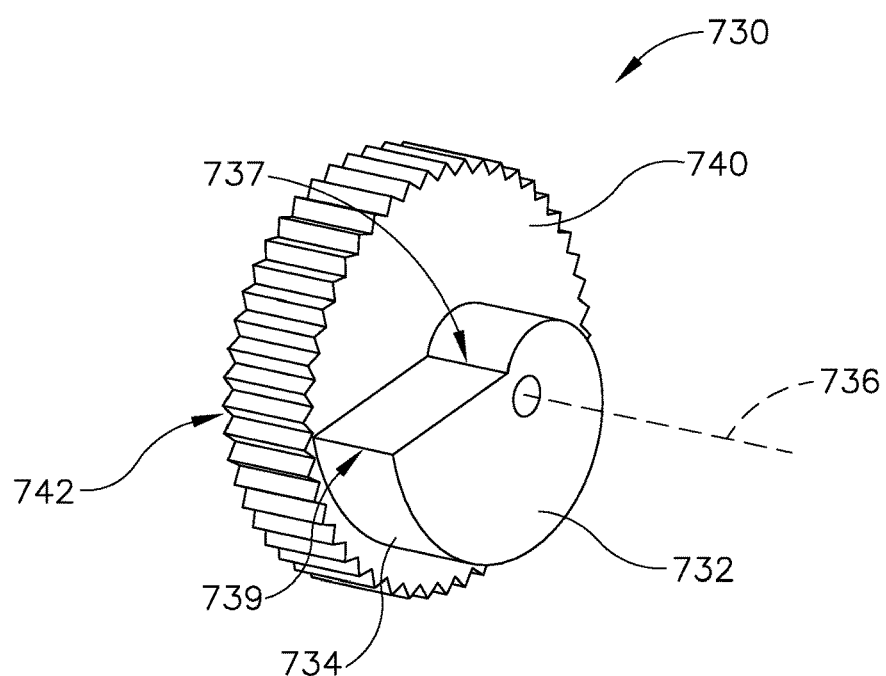
FIG. 23 depicts another perspective view of the rotary drive member of FIG. 22.

As best seen in FIGS. 22-23, rotary drive member (730) includes a cam feature (732) and a pinion feature (740), which are unitarily secured together. Cam feature (732) includes a curved cam surface (734). Cam surface (734) has a spiral curvature in this example, such that the radius of cam surface (734) from the center axis of rotary drive member (730) increases progressively through an angular range about center axis (736). Cam surface (734) thus has a minimum radius point (737) and a maximum radius point (739). Band (726) is secured to the cam feature (732) at the minimum radius point (737). In some versions, the curvature of cam surface (734) is shaped like a Fibonacci curve. Alternatively, cam surface (734) may have any other suitable curvature.

Referring back to FIG. 21, plunger driver (750) of the present example comprises a shaft (752) and a coupling feature (754) at the distal end of shaft (752). Shaft (752) also includes a set of teeth (756) that are configured to mesh with complementary teeth (742) of pinion feature (740) of rotary drive member (730). Shaft (752) and pinion feature (740) thus form a rack and pinion relationship, such that rotation of drive member (730) provides linear translation of plunger driver (750) as will be described in greater detail below.

FIGS. 24A-24B show conventional syringe components coupled with inflator (700). In particular, a flange (762) of a syringe barrel (760) is disposed in annular recess (714) of body (710), thereby coupling syringe barrel (760) with body (710). Syringe barrel (760) may be coupled with port (26) via tube (46) in accordance with the teachings herein. A syringe plunger (770) includes a stem (774) extending between a piston head (not shown) and a push head (772). The piston head is slidably disposed within syringe barrel (760) as described above. Push head (772) is coupled with coupling feature (754) of plunger driver (750) such that plunger (770) and plunger driver (750) translate unitarily within bore (712) of body (710). Various suitable ways in which coupling feature (754) may couple with push head (772) will be apparent to those of ordinary skill in the art in view of the teachings herein. Similarly, various suitable ways in which flange (762) may couple with annular recess (714) will be apparent to those of ordinary skill in the art in view of the teachings herein.

As seen in the transition from FIG. 24A to FIG. 24B, actuator (720) is operable to advance relative to body (710) to drive plunger (770) into syringe barrel (760). In particular, as actuator (720) is advanced distally from the position shown in FIG. 24A to the position shown in FIG. 24B, band (726) acts against cam surface (734) to rotate drive member (730) clockwise (when viewed from the perspective of FIGS. 24A-24B) about center axis (736). Since cam feature (732) and pinion feature (740) rotate together unitarily, and since teeth (742) of pinion feature (740) are engaged with teeth (756) of plunger driver (750), the clockwise rotation of drive member (730) causes distal advancement of plunger driver (750). The distal advancement of plunger driver (750) drives plunger (770) distally into syringe barrel (760), thereby driving fluid from syringe barrel (760) to inflate dilator (22). To deflate dilator (22), plunger driver (750) may be driven proximally, with concurrent counterclockwise rotation of drive member (730). By way of example only, a torsion spring may be used to provide a counterclockwise bias to drive member (730), such that the torsion spring will actuate drive member (730) counterclockwise (and thereby retract plunger driver (750) proximally) when the operator relieves distal force on head (724) of actuator (720). As another merely illustrative example, a coil spring may be used to provide a proximal bias to plunger driver (750), which may in turn provide a counterclockwise bias to drive member (730). Other suitable ways in which one or more features of inflator assembly (700) may be biased will be apparent to those of ordinary skill in the art in view of the teachings herein.

It should be understood that the spiral curvature of cam surface (734) may provide a varying mechanical advantage during distal advancement of actuator (720). For instance, during the initial phases of the transition from the state shown in FIG. 24A to the state shown in FIG. 24B, inflator assembly (700) pay drive a relatively high volume of fluid from syringe barrel (760) at a relatively low mechanical advantage; while during later phases of the transition from the state shown in FIG. 24A to the state shown in FIG. 24B, inflator assembly (700) pay drive a relatively low volume of fluid from syringe barrel (760) at a relatively high mechanical advantage. In other words, during the actuation stroke of actuator (720), the rate of fluid volume transfer from syringe barrel (760) may decrease while the mechanical advantage provided by drive member (730) increases. It should also be understood that the conventional syringe barrel (760) and plunger (770) of the present example are merely illustrative examples. Inflator (700) may be modified to cooperate with various other kinds of components; and may include an integral functional equivalent of syringe barrel (760) and/or plunger (770).

G. Exemplary Inflator with Pre-Charged Drive Cartridge

FIGS. 25A-26B show another exemplary inflator assembly (800) that may be readily incorporated into dilation catheter system (10) in place of inflator (40). Inflator assembly (800) of this example comprises a body (810), a valve assembly (850), and a compressed gas cartridge (890). Body (810) defines a ventilation opening (812), a liquid reservoir (820), and an gas reservoir (824). A plunger (830) extends between reservoirs (820, 824). Plunger (830) includes a stem (832) with a first piston head (834) on one end and a second piston head (836) on another end. First piston head (834) is movable within body (810) to selectively vary a volume of liquid reservoir (820). Second piston head (836) is movable within body (810) to selectively vary a volume of gas reservoir (824). It should be understood that, as the volume of gas reservoir (824) increases, the volume of liquid reservoir (820) decreases due to downward movement of plunger (830). Likewise, as the volume of liquid reservoir (820) increases, the volume of gas reservoir (824) decreases due to upward movement of plunger (830). A coil spring (822) is positioned in liquid reservoir (820), providing an upward resilient bias to plunger (830).

Gas cartridge (890) is configured to hold air or any other gas in a compressed state. In some versions, gas cartridge (890) comprises a conventional compressed $CO_2$ cartridge. It should also be understood that body (810) may be configured to removably receive gas cartridge (890), such that a spent gas cartridge (890) may be replaced with a charged gas cartridge (890). As will be described in greater detail below, the compressed gas in gas cartridge (890) is operable to drive plunger (830) distally, thereby expelling liquid from reservoir (820) through tube (46) to inflate dilator (22).

Figure 26A:
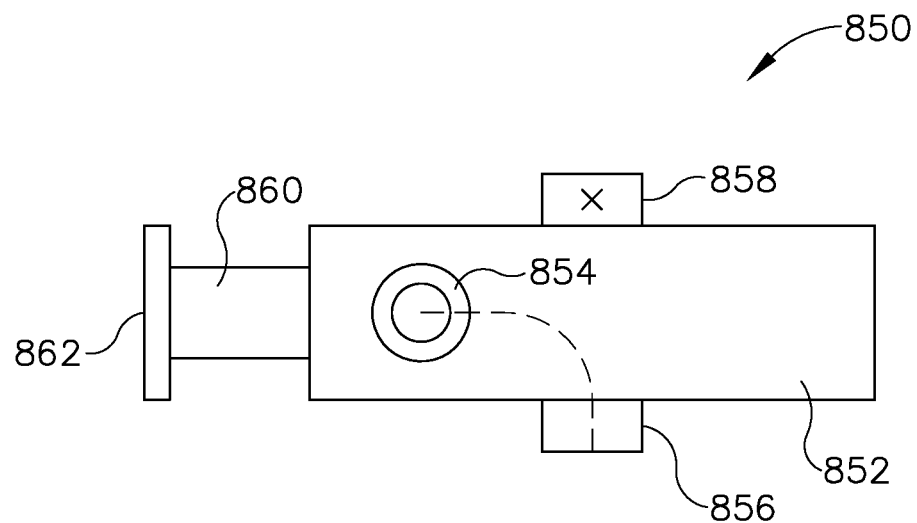
FIG. 26A depicts a side elevational view of a valve assembly of the inflator of FIG. 25A, with the valve assembly in a non-actuated state.
Figure 26B:
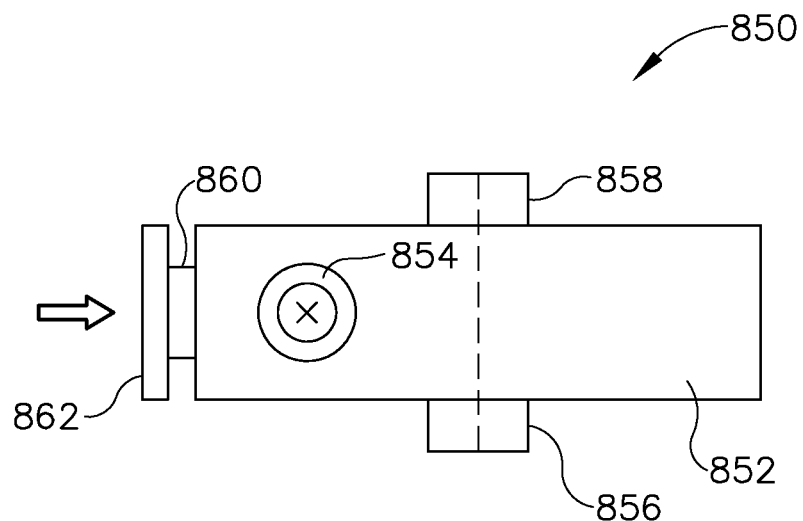
FIG. 26B depicts a side elevational view of the valve assembly of FIG. 26A, with the valve assembly in an actuated state.

Valve assembly (850) of the present example is operable to selectively couple gas reservoir (824) with either gas cartridge (890) or atmospheric air via vent opening (812). FIGS. 26A-26B show an exemplary form that valve assembly (850) may take. In particular, valve assembly (850) of this example comprises a valve body (852) that has three ports (854, 856, 858). A valve actuator (860) is slidably disposed in valve body (852). Valve actuator (860) includes a pushbutton feature (862) that is exposed relative to body (810) such that an operator may readily depress pushbutton feature (862) to transition valve actuator (860) from a non-actuated state (as shown in FIG. 26A) to an actuated state (as shown in FIG. 26B). In some versions, a resilient member (e.g., coil spring, etc.) resiliently biases valve actuator (860) to the non-actuated state, such that valve actuator (860) will return to the non-actuated position when the operator releases pushbutton feature (862).

First port (854) of valve body (852) is in fluid communication with vent opening (812). Second port (856) of valve body (852) is in fluid communication with gas reservoir (824). Third port (858) of valve body is in fluid communication with gas cartridge (890). Valve actuator (860) is configured to provide a fluid path between first port (854) and second port (856) when valve actuator (860) is in the non-actuated state shown in FIG. 26A. In other words, valve assembly (850) vents gas reservoir (824) to atmospheric air when valve actuator (860) is in the non-actuated state. Third port (858) is in fluid isolation when valve actuator (860) is in the non-actuated state, such that no compressed gas is released from gas cartridge (890) when valve actuator (860) is in the non-actuated state. When valve actuator (860) is transitioned to the actuated state shown in FIG. 26B, valve actuator (860) provides a fluid path between second port (856) and third port (858). In other words, valve actuator (860) allows compressed gas to flow from gas cartridge (890) into gas reservoir (824) when valve actuator (860) is in the actuated state. First port (854) is in fluid isolation when valve actuator (860) is in the actuated state. In some versions, valve actuator (860) is configured similar to a translating valve of a trumpet. Other suitable ways in which valve actuator (860) and other components of valve assembly (850) may be configured will be apparent to those of ordinary skill in the art in view of the teachings herein.

Figure 25A:
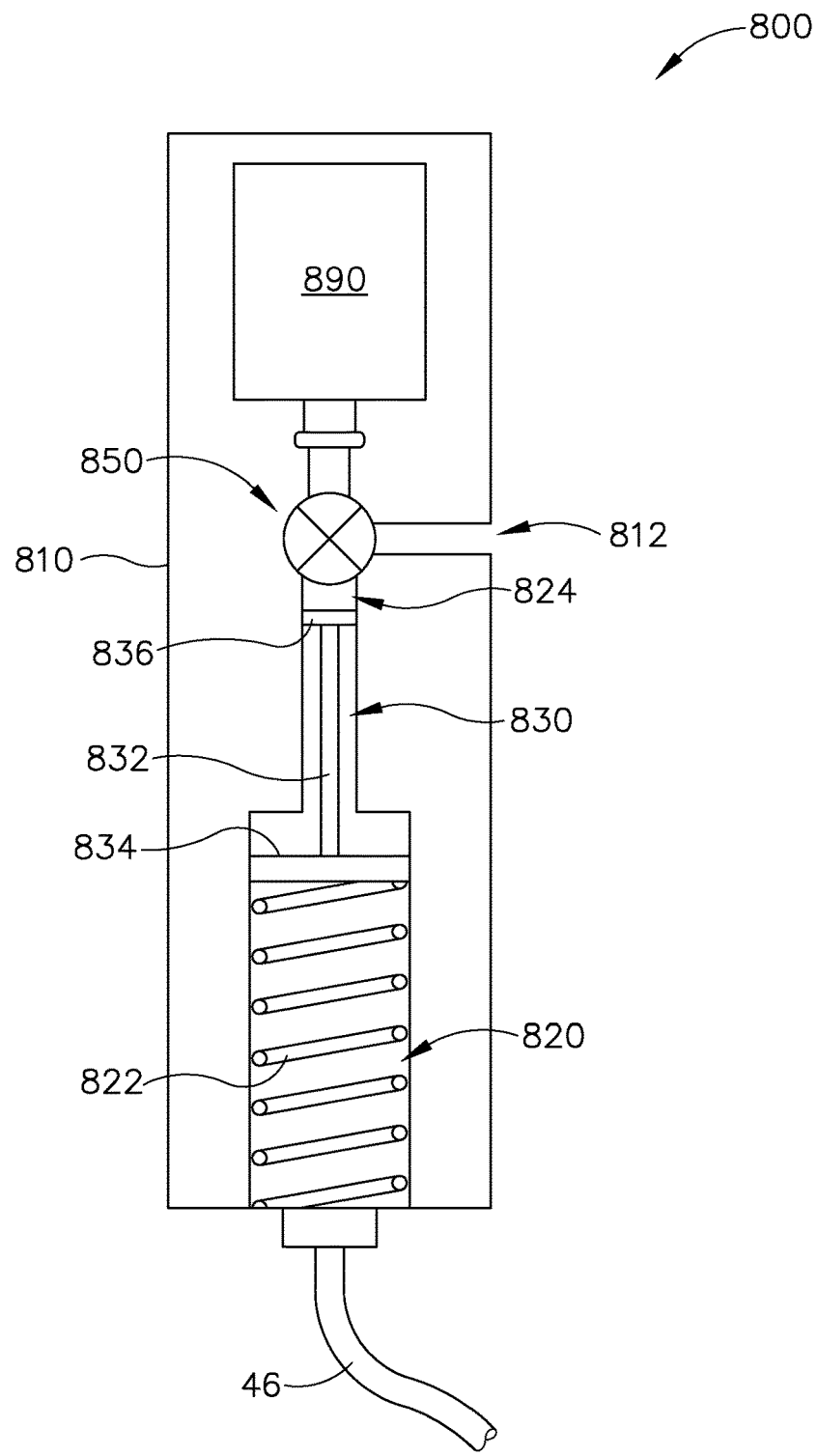
FIG. 25A depicts a schematic view of another exemplary inflator suited for use with the dilator catheter system of FIG. 1, with the inflator in a non-actuated state.
Figure 25B:
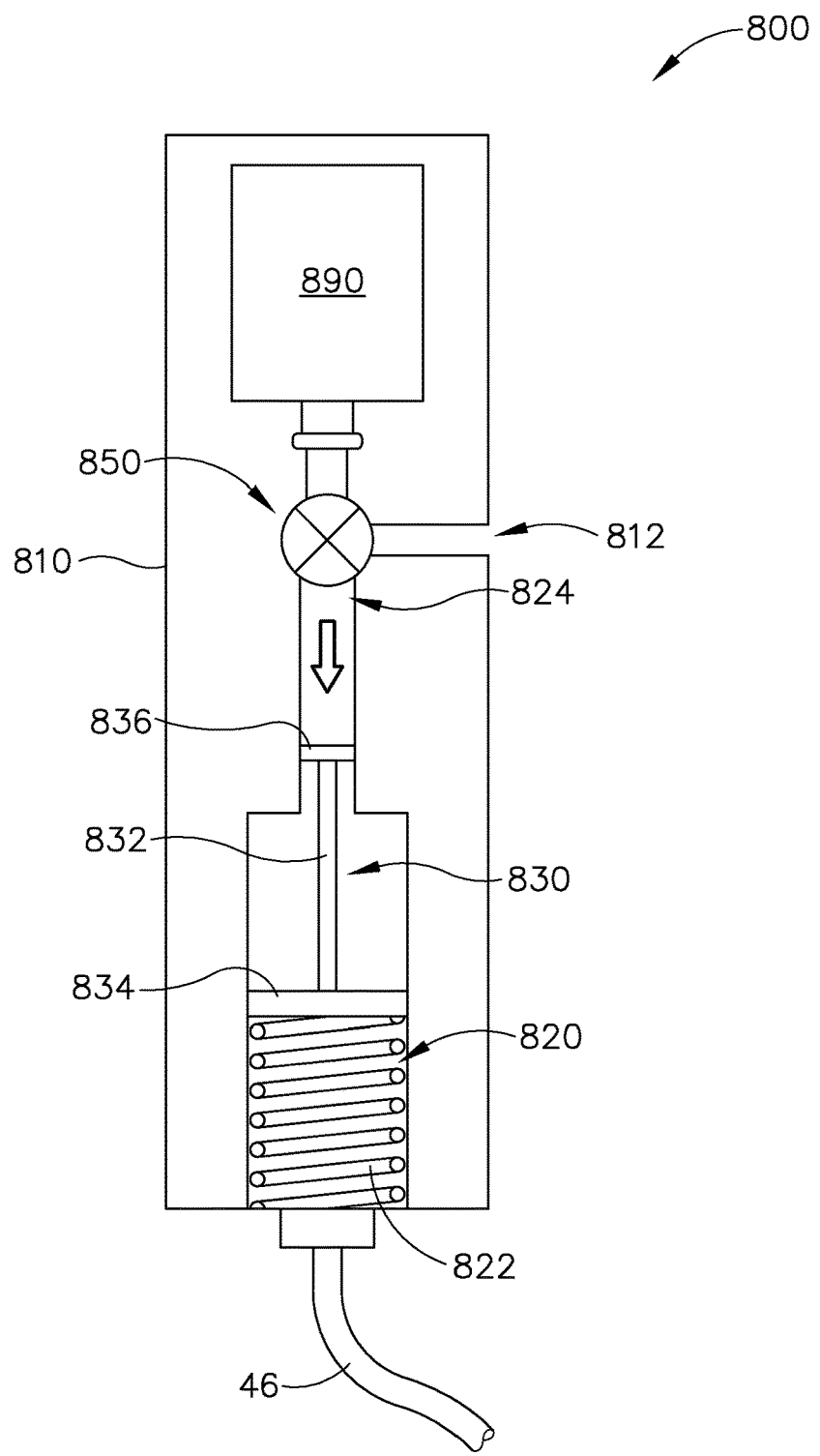
FIG. 25B depicts a schematic view of the inflator of FIG. 25A, with the inflator in an actuated state.

It should be understood from the foregoing that an operator may start with inflator assembly (800) in the configuration shown in FIG. 25A, with valve assembly (850) in the configuration shown in FIG. 26A. The operator may then depress pushbutton feature (862) to place valve assembly (850) in the configuration shown in FIG. 26B. This will allow compressed gas to flow from gas cartridge (890) into gas reservoir (824). Pressure from the compressed gas will bear against second piston head (836), thereby driving plunger (830) distally. First piston head (834) will drive liquid from liquid reservoir (820) toward dilator (22) via tube (46), thereby inflating dilator. First piston head (834) will also compress coil spring (822) at this stage. When the operator is ready to deflate dilator (22), the operator may release pushbutton feature (862). A resilient member of valve assembly (850) may cause valve assembly (850) to return to the configuration shown in FIG. 26A. Upon returning to the configuration shown in FIG. 26A, valve assembly (850) will effectively seal off gas cartridge (890). Valve assembly (850) will also vent gas reservoir (824) to atmospheric air. At this stage, coil spring (820) will bear against first piston head (834) and thereby drive plunger (830) proximally. This proximal movement of plunger (830) will draw liquid back into liquid reservoir (820) via tube (46), thereby deflating dilator (22). Second piston head (836) will drive gas from gas reservoir (824) and out through vent opening (812) as plunger (830) translates proximally. The above process may be repeated as many times as desired.

It should be understood that inflator assembly (800) may be configured in various ways to restrict the fluid pressure imposed on the liquid that is driven by plunger (830), thereby restricting the fluid pressure that may be achieved in dilator (22). For instance, gas reservoir (824) may be configured to provide a particular maximum inflation pressure. In addition or in the alternative, inflator assembly (800) may include a pressure relief valve and/or other pressure restriction feature. It should also be understood that gas cartridge (890) may be replaced with a deformable reservoir (e.g., bellows, bladder, etc.) that is driven by a spring, motor, and/or other source of power. Still other suitable variations of inflator assembly (800) will be apparent to those of ordinary skill in the art in view of the teachings herein.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An inflator, comprising:
   (a) a body defining a reservoir, wherein the reservoir is configured to hold a fluid, wherein the reservoir includes a fluid outlet;
   (b) a first drive member movably engaged with the body, wherein the first drive member is operable to move through the reservoir to selectively drive fluid from the reservoir through the outlet;
   (c) a second drive member engaged with the first drive member; and
   (d) a rotary drive member coupling the first drive member with the second drive member,
   wherein the second drive member is movable distally along an axis relative to the body through a first range of motion to actuate the first drive member to drive fluid through the outlet at a first rate,
   wherein the second drive member is movable distally along the axis relative to the body through a second range of motion following the first range of motion,
   wherein the first drive member is configured to either drive fluid through the outlet at a second rate or not drive fluid through the outlet as the second drive member moves through the second range of motion,
   wherein the rotary drive member is configured to provide displacement of the first drive member relative to the reservoir at the first rate and at a first amount of mechanical advantage as the second drive member moves through the first range of motion, followed by displacement of the first drive member relative to the reservoir at the second rate and at a second amount of mechanical advantage as the second drive member moves through the second range of motion.

2. The inflator of claim 1, wherein the second drive member is further movable relative to the first drive member through the second range of motion.

3. The inflator of claim 1, wherein the second drive member comprises a first ratcheting feature, wherein the body comprises a second ratcheting feature, wherein the first and second ratcheting features are configured to cooperate to selectively maintain longitudinal positioning of the second drive member relative to the body.

4. The inflator of claim 1, further comprising a fluid pressure regulator, wherein the fluid pressure regulator is operable to selectively restrict the pressure of fluid in the reservoir.

5. The inflator of claim 1, wherein the first drive member comprises:
   (i) a plunger, and
   (ii) a plunger driver coupled with the plunger.

6. The inflator of claim 1, wherein the first rate is greater than the second rate.

7. The inflator of claim 1, wherein the second amount of mechanical advantage is greater than the first amount of mechanical advantage.

8. The inflator of claim 1, wherein the rotary drive member comprises a curved cam feature and a set of teeth, wherein the first drive member is engaged with the teeth, wherein the second drive member is engaged with the curved cam feature.

9. The inflator of claim 8, further comprising a flexible band, wherein the second drive member is engaged with the curved cam feature via the flexible band.

10. The inflator of claim 8, wherein the curved cam feature has a spiral curvature.

11. The inflator of claim 1, wherein the second drive member is configured to move continuously through the first range of motion followed by the second range of motion.

12. An inflator, comprising:
    (a) a body defining a reservoir, wherein the reservoir is configured to hold a fluid, wherein the reservoir includes a fluid outlet;
    (b) a first translating drive member movably engaged with the body, wherein the first translating drive member is operable to move through the reservoir to selectively drive fluid from the reservoir through the outlet;
    (c) a second translating drive member engaged with the first translating drive member;
    (d) a rotary drive member coupled with the second translating drive member and configured to rotate about a rotary axis; and
    (e) a flexible band that couples the second translating drive member with the rotary drive member,
    wherein the second translating drive member is configured to translate relative to the body to thereby drive rotation of the rotary drive member about the rotary axis to thereby actuate the first translating drive member to drive fluid through the outlet,
    wherein the first translating drive member is configured to actuate at a varying rate in response to rotation of the rotary drive member about the rotary axis.

13. The inflator of claim 12, wherein the rotary drive member couples the first translating drive member with the second translating drive member.

14. The inflator of claim 12, wherein the rotary drive member includes a gear portion and a toothless cam portion laterally offset from the gear portion, wherein the gear portion is configured to engage the first translating drive member.

15. The inflator of claim 14, wherein the cam portion has a spiral curvature.

16. An inflator, comprising:
    (a) a body defining a reservoir, wherein the reservoir is configured to hold a fluid, wherein the reservoir includes a fluid outlet;
    (b) a first drive member moveably coupled with the body, wherein the first drive member is operable to move through the reservoir to selectively drive fluid from the reservoir through the fluid outlet;
    (c) a second drive member moveable relative to the first drive member;
    (d) a rotary drive member rotatable relative to the second drive member, wherein the rotary drive member operatively couples the first drive member with the second drive member; and
    (e) a flexible band, wherein the flexible band couples the second drive member with the rotary drive member, wherein the flexible band is operable to flex from a first state to a second state to thereby transmit a driving force from the second drive member to the rotary drive member, wherein the rotary drive member is operable to transmit at least a portion of the driving force to the first drive member to thereby drive fluid through the fluid outlet.

17. The inflator of claim 16, wherein the first drive member comprises a first translating drive member, wherein the second drive member comprises a second translating drive member.

18. The inflator of claim 17, wherein a first end of the flexible band is secured to the second translating drive member, wherein a second end of the flexible band is secured to the rotary drive member.

19. The inflator of claim 16, wherein the rotary drive member comprises a cam feature, wherein the flexible band is secured to the cam feature.

20. The inflator of claim 16, wherein the rotary drive member is configured to provide displacement of the first drive member relative to the reservoir at a first rate and with a first amount of mechanical advantage through a first range of motion of the first drive member, wherein the rotary drive member is further configured to provide displacement of the first drive member relative to the reservoir at a second rate and with a second amount of mechanical advantage through a second range of motion of the first drive member, wherein the second range of motion follows the first range of motion.

* * * * *